(12) United States Patent
Kilgore et al.

(10) Patent No.: US 9,732,300 B2
(45) Date of Patent: Aug. 15, 2017

(54) LIQUID PROPYLENE OLIGOMERS AND METHODS OF MAKING SAME

(71) Applicant: Chevron Phillips Chemical Company LP, The Woodlands, TX (US)

(72) Inventors: Uriah J. Kilgore, Kingwood, TX (US); Graham R. Lief, Bartlesville, OK (US); Eric J. Haschke, Bartlesville, OK (US)

(73) Assignee: Chevron Phillipa Chemical Company LP, The Woodlands, TX (US)

( * ) Notice: Subject to any disclaimer, the term of this patent is extended or adjusted under 35 U.S.C. 154(b) by 14 days.

(21) Appl. No.: 14/806,708

(22) Filed: Jul. 23, 2015

(65) Prior Publication Data

US 2017/0022439 A1   Jan. 26, 2017

(51) Int. Cl.
*C10M 105/04* (2006.01)
*C10G 50/02* (2006.01)
*C07C 2/08* (2006.01)
*C08F 10/06* (2006.01)

(52) U.S. Cl.
CPC ............ *C10M 105/04* (2013.01); *C10G 50/02* (2013.01); *C07C 2/08* (2013.01); *C08F 10/06* (2013.01); *C10M 2203/02* (2013.01); *C10M 2205/024* (2013.01)

(58) Field of Classification Search
CPC ...... C10G 50/00; C10G 50/02; C10M 105/04; C10M 2203/02
USPC ........................................ 585/1–27, 510–533
See application file for complete search history.

(56) References Cited

U.S. PATENT DOCUMENTS

| | | |
|---|---|---|
| 1,815,022 A | 7/1931 | Davis |
| 2,015,748 A | 10/1935 | Frolich |
| 2,191,498 A | 2/1940 | Reiff |
| 2,387,501 A | 10/1945 | Dietrich |
| 2,443,264 A | 6/1948 | Mikeska |
| 2,655,479 A | 1/1949 | Munday et al. |
| 2,471,115 A | 5/1949 | Mikeska |
| 2,526,497 A | 10/1950 | Mikeska |
| 2,591,577 A | 1/1952 | McDermott |
| 2,666,746 A | 1/1954 | Munday et al. |
| 2,719,125 A | 9/1955 | Roberts |
| 2,719,126 A | 9/1955 | Fields et al. |
| 2,721,877 A | 10/1955 | Popkin et al. |
| 2,721,878 A | 10/1955 | Popkin |
| 3,036,003 A | 5/1962 | Verdol et al. |
| 3,087,932 A | 4/1963 | Little, Jr. |
| 3,087,936 A | 4/1963 | Le Suer et al. |
| 3,172,892 A | 3/1965 | Le Suer et al. |
| 3,200,107 A | 8/1965 | Le Suer et al. |
| 3,214,570 A | 10/1965 | Wray, Jr. |
| 3,219,666 A | 11/1965 | Norman et al. |
| 3,242,099 A | 3/1966 | Manyik et al. |

(Continued)

FOREIGN PATENT DOCUMENTS

EP    0 490 454    6/1992

*Primary Examiner* — Ellen McAvoy
(74) *Attorney, Agent, or Firm* — Merchant & Gould P.C.

(57) ABSTRACT

Disclosed herein are oligomerization processes using feedstocks containing propylene to produce an oligomer product, and methods for recovering a propylene oligomer from the oligomer product. The resultant propylene oligomer can be characterized by a Mn in a range from 250 to 10,000 g/mol, a viscosity index of at least 85, and a pour point in a range from −5 to −60° C.

25 Claims, 1 Drawing Sheet

(56) References Cited

U.S. PATENT DOCUMENTS

| | | | |
|---|---|---|---|
| 3,250,715 | A | 5/1966 | Wyman |
| 3,254,025 | A | 5/1966 | Le Suer et al. |
| 3,272,746 | A | 9/1966 | Le Suer et al. |
| 3,275,554 | A | 9/1966 | Wagenaar et al. |
| 3,316,177 | A | 4/1967 | Dorer, Jr. |
| 3,322,670 | A | 5/1967 | Burt et al. |
| 3,329,658 | A | 7/1967 | Fields |
| 3,341,542 | A | 9/1967 | Le Suer et al. |
| 3,413,347 | A | 11/1968 | Worrel |
| 3,438,757 | A | 4/1969 | Honnen et al. |
| 3,444,170 | A | 5/1969 | Norman et al. |
| 3,449,250 | A | 6/1969 | Fields |
| 3,454,555 | A | 7/1969 | van der Voort et al. |
| 3,454,607 | A | 7/1969 | Le Suer et al. |
| 3,519,565 | A | 7/1970 | Coleman |
| 3,541,012 | A | 11/1970 | Stuebe |
| 3,565,804 | A | 2/1971 | Honnen et al. |
| 3,630,904 | A | 12/1971 | Musser et al. |
| 3,632,511 | A | 1/1972 | Liao |
| 3,652,616 | A | 3/1972 | Watson et al. |
| 3,666,730 | A | 5/1972 | Coleman |
| 3,687,849 | A | 8/1972 | Abbott |
| 3,697,574 | A | 10/1972 | Piasek et al. |
| 3,702,300 | A | 11/1972 | Coleman |
| 3,703,536 | A | 11/1972 | Piasek et al. |
| 3,704,308 | A | 11/1972 | Piasek et al. |
| 3,725,277 | A | 4/1973 | Worrel |
| 3,725,480 | A | 4/1973 | Traise et al. |
| 3,726,882 | A | 4/1973 | Traise et al. |
| 3,751,365 | A | 8/1973 | Piasek et al. |
| 3,755,433 | A | 8/1973 | Miller et al. |
| 3,756,953 | A | 9/1973 | Piasek et al. |
| 3,770,854 | A | 11/1973 | Morris et al. |
| 3,787,374 | A | 1/1974 | Adams |
| 3,798,165 | A | 3/1974 | Piasek et al. |
| 3,803,039 | A | 4/1974 | Piasek et al. |
| 3,822,209 | A | 7/1974 | Knapp et al. |
| 3,948,800 | A | 4/1976 | Meinhardt |
| 4,100,082 | A | 7/1978 | Clason et al. |
| 4,234,435 | A | 11/1980 | Meinhardt et al. |
| 4,426,305 | A | 1/1984 | Malec |
| 4,454,059 | A | 6/1984 | Pindar et al. |
| 4,501,678 | A | 2/1985 | Katayama et al. |
| 4,668,838 | A | 5/1987 | Briggs |
| 4,767,551 | A | 8/1988 | Hunt et al. |
| 4,777,315 | A | 10/1988 | Levine et al. |
| 4,794,096 | A | 12/1988 | Ewen |
| 4,798,684 | A | 1/1989 | Salomon |
| 4,808,561 | A | 2/1989 | Welborn, Jr. |
| 4,814,540 | A | 3/1989 | Watanabe et al. |
| 4,853,356 | A | 8/1989 | Briggs |
| 4,941,984 | A | 7/1990 | Chamberlin, III et al. |
| 5,034,141 | A | 7/1991 | Beltzer et al. |
| 5,034,142 | A | 7/1991 | Habeeb et al. |
| 5,049,535 | A | 9/1991 | Resconi et al. |
| 5,084,197 | A | 1/1992 | Galic et al. |
| 5,171,919 | A | 12/1992 | Watanabe et al. |
| 5,177,276 | A | 1/1993 | Beach et al. |
| 5,182,333 | A | 1/1993 | Powers et al. |
| 5,198,563 | A | 3/1993 | Reagen et al. |
| 5,288,823 | A | 2/1994 | Reagan et al. |
| 5,321,189 | A | 6/1994 | Mueller et al. |
| 5,329,031 | A | 7/1994 | Miyake et al. |
| 5,331,104 | A | 7/1994 | Reagen et al. |
| 5,340,785 | A | 8/1994 | Reagen et al. |
| 5,349,032 | A | 9/1994 | Miyake et al. |
| 5,360,879 | A | 11/1994 | Reagen et al. |
| 5,376,612 | A | 12/1994 | Reagen et al. |
| 5,382,738 | A | 1/1995 | Reagen et al. |
| 5,399,539 | A | 3/1995 | Reagen et al. |
| 5,416,179 | A | 5/1995 | Welch et al. |
| 5,433,875 | A | 7/1995 | Rollin et al. |
| 5,438,027 | A | 8/1995 | Reagen et al. |
| 5,470,926 | A | 11/1995 | Reagen et al. |
| 5,523,507 | A | 6/1996 | Reagen et al. |
| 5,543,373 | A | 8/1996 | Winter et al. |
| 5,543,375 | A | 8/1996 | Lashier et al. |
| 5,563,312 | A | 10/1996 | Knudsen et al. |
| 5,576,259 | A | 11/1996 | Hasegawa et al. |
| 5,616,153 | A | 4/1997 | Mike et al. |
| 5,675,049 | A | 10/1997 | Vermeiren et al. |
| 5,688,887 | A | 11/1997 | Bagheri et al. |
| 5,689,028 | A | 11/1997 | Lashier et al. |
| 5,693,598 | A | 12/1997 | Abraham et al. |
| 5,705,458 | A | 1/1998 | Roby et al. |
| 5,736,492 | A | 4/1998 | Clark et al. |
| 5,741,868 | A | 4/1998 | Winter et al. |
| 5,750,816 | A | 5/1998 | Araki et al. |
| 5,756,609 | A | 5/1998 | Cohen |
| 5,763,723 | A | 6/1998 | Reagen et al. |
| 5,807,938 | A | 9/1998 | Kaneko et al. |
| 5,814,575 | A | 9/1998 | Reagen et al. |
| 5,831,106 | A | 11/1998 | Langhauser et al. |
| 5,840,947 | A | 11/1998 | Kuber et al. |
| 5,856,257 | A | 1/1999 | Freeman et al. |
| 5,856,612 | A | 1/1999 | Araki et al. |
| 5,859,303 | A | 1/1999 | Lashier |
| 5,908,903 | A | 6/1999 | Rösch |
| 5,910,619 | A | 6/1999 | Urata et al. |
| 5,919,983 | A | 7/1999 | Rosen et al. |
| 6,043,401 | A | 3/2000 | Bagheri et al. |
| 6,107,230 | A | 8/2000 | McDaniel et al. |
| 6,121,394 | A | 9/2000 | Sugimoto et al. |
| 6,124,513 | A | 9/2000 | Heilman et al. |
| 6,133,495 | A | 10/2000 | Urata et al. |
| 6,153,549 | A | 11/2000 | Hubscher et al. |
| 6,165,929 | A | 12/2000 | McDaniel et al. |
| 6,169,051 | B1 | 1/2001 | Mitani et al. |
| 6,191,294 | B1 | 2/2001 | Resconi et al. |
| 6,239,059 | B1 | 5/2001 | Saudemont et al. |
| 6,255,417 | B1 | 7/2001 | Oh et al. |
| 6,265,339 | B1 | 7/2001 | Bidell et al. |
| 6,294,494 | B1 | 9/2001 | McDaniel et al. |
| 6,300,271 | B1 | 10/2001 | McDaniel et al. |
| 6,316,553 | B1 | 11/2001 | McDaniel et al. |
| 6,326,493 | B1 | 12/2001 | Mitani et al. |
| 6,355,594 | B1 | 3/2002 | McDaniel et al. |
| 6,365,763 | B1 | 4/2002 | Winter et al. |
| 6,376,415 | B1 | 4/2002 | McDaniel et al. |
| 6,380,451 | B1 | 4/2002 | Kreischer et al. |
| 6,388,017 | B1 | 5/2002 | McDaniel et al. |
| 6,391,816 | B1 | 5/2002 | McDaniel et al. |
| 6,395,666 | B1 | 5/2002 | McDaniel et al. |
| 6,423,660 | B1 | 7/2002 | Albizzati et al. |
| 6,444,604 | B1 | 9/2002 | Albizzati et al. |
| 6,444,607 | B1 | 9/2002 | Gonioukh et al. |
| 6,455,648 | B1 | 9/2002 | Freeman et al. |
| 6,458,904 | B1 | 10/2002 | Gonioukh et al. |
| 6,524,987 | B1 | 2/2003 | Collins et al. |
| 6,524,988 | B2 | 2/2003 | Speca |
| 6,548,441 | B1 | 4/2003 | McDaniel et al. |
| 6,548,442 | B1 | 4/2003 | McDaniel et al. |
| 6,548,723 | B2 | 4/2003 | Bagheri et al. |
| 6,573,352 | B1 * | 6/2003 | Tatsumi ............... C08F 10/06 526/348.2 |
| 6,576,583 | B1 | 6/2003 | McDaniel et al. |
| 6,613,712 | B1 | 9/2003 | McDaniel et al. |
| 6,632,894 | B1 | 10/2003 | McDaniel et al. |
| 6,632,901 | B2 | 10/2003 | McCullough |
| 6,667,274 | B1 | 12/2003 | Hawley et al. |
| 6,706,828 | B2 | 3/2004 | Dimaio |
| 6,720,396 | B2 | 4/2004 | Bell et al. |
| 6,750,302 | B1 | 6/2004 | McDaniel et al. |
| 6,774,194 | B2 | 8/2004 | Albizzati et al. |
| 6,831,141 | B2 | 12/2004 | McDaniel et al. |
| 6,858,767 | B1 | 2/2005 | DiMaio et al. |
| 6,878,785 | B2 | 4/2005 | McDaniel et al. |
| 6,936,667 | B2 | 8/2005 | Jensen et al. |
| 6,992,032 | B2 | 1/2006 | McDaniel et al. |
| 6,995,279 | B2 | 2/2006 | Ushioda et al. |
| 7,026,494 | B1 | 4/2006 | Yang et al. |
| 7,041,617 | B2 | 5/2006 | Jensen et al. |
| 7,109,277 | B2 | 9/2006 | Hawley et al. |
| 7,129,306 | B2 | 10/2006 | Dimaio |

(56) References Cited

U.S. PATENT DOCUMENTS

| | | | |
|---|---|---|---|
| 7,132,382 | B2 | 11/2006 | McCullough |
| 7,148,298 | B2 | 12/2006 | Jensen et al. |
| 7,157,612 | B2 | 1/2007 | Ewert et al. |
| 7,163,906 | B2 | 1/2007 | McDaniel et al. |
| 7,199,073 | B2 | 4/2007 | Martin et al. |
| 7,226,886 | B2 | 6/2007 | Jayaratne et al. |
| 7,271,277 | B2 | 9/2007 | Park et al. |
| 7,285,513 | B2 | 10/2007 | Kratzer et al. |
| 7,285,607 | B2 | 10/2007 | Blann et al. |
| 7,294,599 | B2 | 11/2007 | Jensen et al. |
| 7,297,832 | B2 | 11/2007 | Blann et al. |
| 7,312,283 | B2 | 12/2007 | Martin et al. |
| 7,323,524 | B2 | 1/2008 | Blann et al. |
| 7,378,537 | B2 | 5/2008 | Small et al. |
| 7,384,886 | B2 | 6/2008 | Knudsen et al. |
| 7,439,378 | B2 | 10/2008 | Park et al. |
| 7,468,451 | B2 | 12/2008 | Guidotti et al. |
| 7,470,758 | B2 | 12/2008 | Jensen et al. |
| 7,476,775 | B2 | 1/2009 | Kreischer |
| 7,501,372 | B2 | 3/2009 | Thorn et al. |
| 7,511,183 | B2 | 3/2009 | Blann et al. |
| 7,517,939 | B2 | 4/2009 | Yang et al. |
| 7,525,009 | B2 | 4/2009 | Blann et al. |
| 7,527,686 | B2 | 5/2009 | Yang et al. |
| 7,576,163 | B2 | 8/2009 | Yang et al. |
| 7,601,665 | B2 | 10/2009 | McDaniel et al. |
| 7,619,047 | B2 | 11/2009 | Yang et al. |
| 7,629,284 | B2 | 12/2009 | Jensen et al. |
| 7,652,160 | B2 | 1/2010 | Yang et al. |
| 7,662,895 | B2 * | 2/2010 | Brant ............... C08F 110/06 525/240 |
| 7,718,838 | B2 | 5/2010 | Woodard et al. |
| 7,820,581 | B2 | 10/2010 | Knudsen et al. |
| 7,828,957 | B2 | 11/2010 | Yang et al. |
| 7,829,749 | B2 | 11/2010 | Gao et al. |
| 7,884,163 | B2 | 2/2011 | McDaniel et al. |
| 7,906,681 | B2 | 3/2011 | Gao et al. |
| 7,910,670 | B2 | 3/2011 | Knudsen et al. |
| 7,919,639 | B2 | 4/2011 | Murray et al. |
| 7,964,763 | B2 | 6/2011 | Dixon et al. |
| 7,989,670 | B2 * | 8/2011 | Wu ..................... C08F 10/00 585/250 |
| 7,994,363 | B2 | 8/2011 | Gao et al. |
| 8,049,052 | B2 | 11/2011 | Kreischer et al. |
| 8,076,523 | B2 | 12/2011 | Bollmann et al. |
| 8,080,681 | B2 | 12/2011 | Murray et al. |
| 8,101,809 | B2 | 1/2012 | Elomari et al. |
| 8,114,946 | B2 | 2/2012 | Yang et al. |
| 8,124,821 | B2 | 2/2012 | Elomari et al. |
| 8,134,038 | B2 | 3/2012 | McGuinness et al. |
| 8,143,467 | B2 | 3/2012 | Patil et al. |
| 8,178,739 | B2 | 5/2012 | Elomari et al. |
| 8,222,471 | B2 | 7/2012 | Elomari et al. |
| 8,227,392 | B2 * | 7/2012 | Wu ..................... C08F 10/08 508/591 |
| 8,252,955 | B2 | 8/2012 | Gao et al. |
| 8,252,956 | B2 | 8/2012 | Gao et al. |
| 8,268,941 | B2 | 9/2012 | Kleingeld et al. |
| 8,283,428 | B2 | 10/2012 | Brant et al. |
| 8,309,485 | B2 | 11/2012 | Yang et al. |
| 8,318,998 | B2 | 11/2012 | Crowther et al. |
| 8,329,608 | B2 | 12/2012 | Knudsen et al. |
| 8,334,420 | B2 | 12/2012 | Small et al. |
| 8,344,198 | B2 | 1/2013 | Ewert et al. |
| 8,367,786 | B2 | 2/2013 | Dixon et al. |
| 8,372,930 | B2 | 2/2013 | Brant et al. |
| 8,399,724 | B2 | 3/2013 | Crowther et al. |
| 8,399,725 | B2 * | 3/2013 | Brant ............... C08F 210/06 525/340 |
| 8,431,662 | B2 | 4/2013 | Brant et al. |
| 8,455,597 | B2 | 6/2013 | Crowther et al. |
| 8,461,406 | B2 | 6/2013 | Overett et al. |
| 8,471,085 | B2 | 6/2013 | Sydora |
| 8,486,877 | B2 | 7/2013 | Campbell et al. |
| 8,513,478 | B2 * | 8/2013 | Wu ..................... C08F 10/00 585/502 |
| 8,536,391 | B2 | 9/2013 | Small et al. |
| 8,604,258 | B2 | 12/2013 | Elomari et al. |
| 8,623,973 | B1 | 1/2014 | McDaniel et al. |
| 8,623,974 | B2 * | 1/2014 | Jiang ............... C08F 210/06 526/134 |
| 8,680,003 | B2 | 3/2014 | Sydora et al. |
| 8,703,886 | B1 | 4/2014 | Yang et al. |
| 8,779,067 | B2 * | 7/2014 | Brant ............... C08F 210/06 525/333.7 |
| 9,023,959 | B2 | 5/2015 | McDaniel et al. |
| 9,175,109 | B1 | 11/2015 | Kreischer et al. |
| 2008/0146469 | A1 | 6/2008 | Sato et al. |
| 2009/0240012 | A1 | 9/2009 | Patil et al. |
| 2010/0317904 | A1 | 12/2010 | Small |
| 2011/0082323 | A1 | 4/2011 | Small et al. |
| 2012/0172644 | A1 | 7/2012 | Elomari et al. |
| 2014/0179964 | A1 | 6/2014 | Gee |
| 2014/0213745 | A1 * | 7/2014 | Jiang ............... C08F 210/06 526/126 |
| 2015/0025210 | A1 * | 1/2015 | Canich ............... C08F 10/06 526/127 |
| 2015/0099679 | A1 | 4/2015 | Yang et al. |

\* cited by examiner

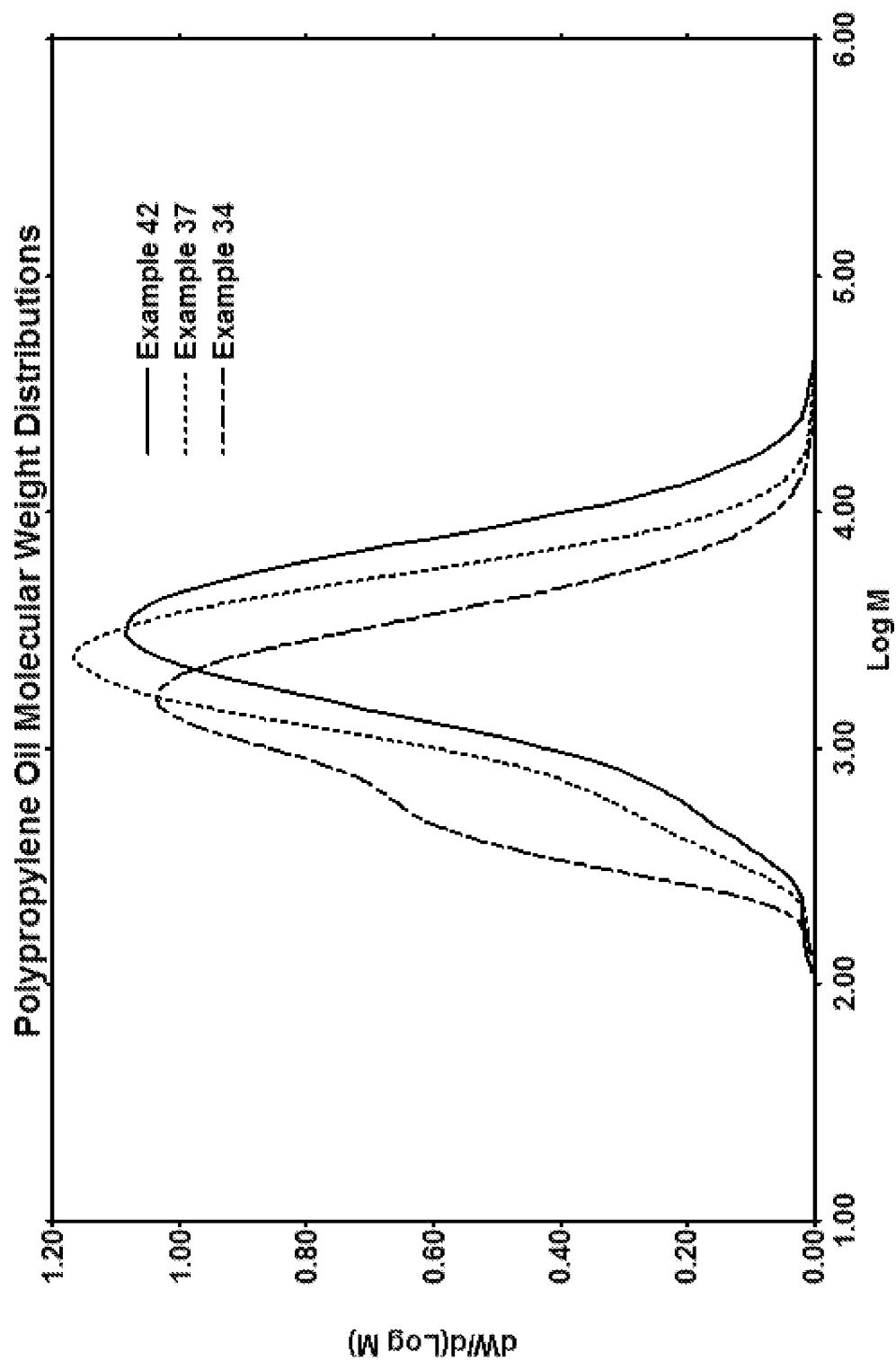

LIQUID PROPYLENE OLIGOMERS AND METHODS OF MAKING SAME

BACKGROUND OF THE INVENTION

The present invention relates generally to processes for oligomerizing propylene with a catalyst system containing a metallocene compound, a chemically-treated solid oxide, and an optional co-catalyst, and to propylene oligomers having specific molecular weight, viscosity index, and pour point characteristics.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Embodiments of this invention are directed to a process comprising contacting a catalyst system with an olefin feedstock comprising propylene to form an oligomer product. The catalyst system can comprise (i) a metallocene compound, (ii) a chemically-treated solid oxide, and (iii) an optional co-catalyst. In some embodiments, the catalyst system and the olefin feedstock can be contacted in the presence of hydrogen. A heavy propylene oligomer can be isolated from the oligomer product, and the heavy propylene oligomer can be used as a base oil, or in lubricants or other compositions.

Propylene oligomers also are disclosed and described herein. A propylene oligomer in one embodiment of this invention can be characterized by a Mn in a range from 250 to 10,000 g/mol, a viscosity index of at least 85, and a pour point in a range from −5 to −60° C. A propylene oligomer in another embodiment of this invention can be characterized by a Mn in a range from 250 to 10,000 g/mol, a ratio of Mz/Mw in a range from 1.9 to 8, and a viscosity index of at least 85. These propylene oligomers, in further embodiments, can be characterized by various molecular weight properties (e.g., Mw, Mw/Mn) and various viscosity properties (e.g., kinematic viscosity at 40° C., kinematic viscosity at 100° C.). The propylene oligomers can be used in base oils, or in lubricants and other compositions.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

BRIEF DESCRIPTION OF THE FIGURE

The FIGURE provides the molecular weight distributions of the propylene oligomers produced in Examples 34, 37, and 42.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features can be envisioned. For each and every aspect, and/or embodiment, and/or feature disclosed herein, all combinations that do not detrimentally affect the designs, compositions, processes, and/or methods described herein are contemplated with or without explicit description of the particular combination. Additionally, unless explicitly recited otherwise, any aspect, and/or embodiment, and/or feature disclosed herein can be combined to describe inventive features consistent with the present disclosure.

Regarding claim transitional terms or phrases, the transitional term "comprising," which is synonymous with "including," "containing," "having," or "characterized by," is open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristics of the claimed invention. A "consisting essentially of" claim occupies a middle ground between closed claims that are written in a "consisting of" format and fully open claims that are drafted in a "comprising" format. Absent an indication to the contrary, describing a composition or method as "consisting essentially of" is not to be construed as "comprising," but is intended to describe the recited element that includes materials or steps which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a product stream consisting of specific components; alternatively, consisting essentially of specific components; or alternatively, comprising the specific components and other non-recited components. While compositions and methods are described in terms of "comprising" various components or steps, the compositions and methods can also "consist essentially of" or "consist of" the various components or steps, unless specifically stated otherwise. For example, a chemically-treated solid oxide consistent with certain embodiments of the present invention can comprise; alternatively, consist essentially of; or alternatively, consist of; a fluorided solid oxide.

The terms "a," "an," and "the" are intended to include plural alternatives, e.g., at least one, unless otherwise specified. For instance, the disclosure of "an additive" or "a separation step" is meant to encompass one, or combinations of more than one, additive or separation step (e.g., a flash process, a distillation process, etc.), respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans,trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

The terms "contact product," "contacting," and the like, are used herein to describe compositions and methods wherein the components are contacted together in any order, in any manner, and for any length of time, unless otherwise specified. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise contacted in some other manner. Hence, "contacting" two or more components can result in a mixture, a reaction product, a reaction mixture, etc.

The term "hydrocarbon" whenever used in this specification and claims refers to a compound containing only carbon and hydrogen. The term "olefin" as used herein refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The terms "oligomerization product" and "oligomer product" include all products made by the "oligomerization" process including the "oligomers" and products which are not "oligomers" (e.g., polymer). As used herein, "propylene oligomer" and "heavy propylene oligomer" typically refer to a propylene oligomer (or composition) having little to no light propylene oligomers, e.g., a propylene oligomer (or composition) where at least a portion of lighter oligomers (such as $C_6$, $C_9$, and $C_{12}$ oligomers), if produced, has been removed from the "oligomer product." The terms "propylene oligomer" and "heavy propylene oligomer" can be used interchangeably, however, the term "heavy propylene oligomer" generally refers to a propylene oligomer (or composition) isolated from a process producing an oligomer product. These terms also can be used generically herein to include propylene homo-oligomers, propylene co-oligomers, and so forth.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The oligomerization of feedstocks containing propylene using a metallocene-based catalyst system containing a chemically-treated solid oxide are disclosed and described herein. Such catalyst systems and processes have unexpectedly improved hydrogen response characteristics, allowing lower molecular weight and lower viscosity oligomers to be produced without the excessive use of hydrogen, as is the case in other oligomerization catalyst systems. Also disclosed herein are propylene oligomers having an unexpected combination of a higher viscosity index and a lower pour point.

Propylene Oligomers

An illustrative and non-limiting example of a propylene oligomer or a heavy propylene oligomer of the present invention can have a Mn in a range from 250 to 10,000 g/mol, a viscosity index of at least 85, and a pour point in a range from −5 to −60° C. Another illustrative and non-limiting example of a propylene oligomer or a heavy propylene oligomer of the present invention can have a Mn in a range from 250 to 10,000 g/mol, a ratio of Mz/Mw in a range from 1.9 to 8, and a viscosity index of at least 85. Yet another illustrative and non-limiting example of a propylene oligomer or a heavy propylene oligomer of the present invention can have a Mn in a range from 500 to 5000 g/mol (or from 500 to 2500 g/mol), a viscosity index in a range from 85 to 175 (or from 88 to 135), and a pour point in a range from −10 to −35° C. (or from −15 to −40° C.). These illustrative and non-limiting examples of the propylene oligomer or the heavy propylene oligomer consistent with the present invention also can have any of the characteristics of the propylene oligomer or the heavy propylene oligomer properties provided below, and in any combination.

The pour point of the propylene oligomer or the heavy propylene oligomer typically can fall within a range from −5 to −60° C. For instance, the minimum pour point of the propylene oligomer can be −60, −50, −45, −40, or −35° C.; additionally or alternatively, the maximum pour point can be −5, −8, −10, −15, or −20° C. Generally, the pour point of the propylene oligomer or the heavy propylene oligomer can be in a range from any minimum pour point temperature disclosed herein to any maximum pour point temperature disclosed herein. Therefore, suitable non-limiting ranges for the pour point of the propylene oligomer or the heavy propylene oligomer can include the following ranges: from −5 to −50° C., from −5 to −45° C., from −8 to −45° C., from −10 to −40° C., from −10 to −35° C., from −15 to −60° C., from −15 to −50° C., or from −15 to −40° C. Other appropriate ranges for the pour point of the propylene oligomer or the heavy propylene oligomer are readily apparent from this disclosure. Generally, the pour point of the propylene oligomer or the heavy propylene oligomer can be measured using ASTM D97-04.

The propylene oligomer or the heavy propylene oligomer can have a viscosity index of greater than 85. For instance, the viscosity index of the propylene oligomer or the heavy propylene oligomer can be at least 85, 86, 87, 88, 89, or 90; additionally or alternatively, the maximum viscosity index can be 200, 175, 150, 140, 135, 130, 125, or 120. Generally, the viscosity index of the propylene oligomer or the heavy propylene oligomer can be in a range from any minimum viscosity index disclosed herein to any maximum viscosity index disclosed herein. Therefore, suitable non-limiting ranges for the viscosity index of the propylene oligomer or the heavy propylene oligomer can include the following ranges: from 85 to 200, from 85 to 175, from 85 to 140, from 85 to 130, from 88 to 150, from 88 to 135, from 90 to 140, or from 90 to 130. Other appropriate ranges for the viscosity index of the propylene oligomer or the heavy propylene oligomer are readily apparent from this disclosure. Generally, the viscosity index of the propylene oligomer or the heavy propylene oligomer can be measured using ASTM D7042-04.

Consistent with embodiments of this invention, the propylene oligomer or the heavy propylene oligomer can have a kinematic viscosity at 40° C. ranging from 25 to 8000 cSt. For instance, the propylene oligomer or the heavy propylene oligomer can have a kinematic viscosity at 40° C. of at least 25, 50, 75, 100, 150, 175, or 200 cSt; additionally or alternatively, the maximum kinematic viscosity at 40° C. of the propylene oligomer or the heavy propylene oligomer can be 8000, 7000, 6000, 5000, 4000, 3000, 2000, 1500, 1000, or 800 cSt. Generally, the kinematic viscosity at 40° C. of the propylene oligomer or the heavy propylene oligomer can be in a range from any minimum kinematic viscosity disclosed herein to any maximum kinematic viscosity disclosed herein. Therefore, suitable non-limiting ranges for the kinematic viscosity at 40° C. of the propylene oligomer or the heavy propylene oligomer can include the following ranges: from 25 to 8000 cSt, from 50 to 6000 cSt, from 75 to 6000 cSt, from 75 to 400 cSt, from 25 to 800 cSt, from 100 to 6000 cSt, from 100 to 4000 cSt, from 150 to 6000 cSt, from 150 to 400 cSt, from 150 to 2000 cSt, from 175 to 2000 cSt, from 175 to 1500 cSt, from 200 to 2000 cSt, from 200 to 1500 cSt, or from 200 to 800 cSt. Other appropriate ranges for the kinematic viscosity at 40° C. of the propylene oligomer or the heavy propylene oligomer are readily apparent from this disclosure.

The propylene oligomer or the heavy propylene oligomer can have a kinematic viscosity at 100° C. that typically ranges from 6 to 200 cSt. For instance, the propylene oligomer or the heavy propylene oligomer can have a kinematic viscosity at 100° C. of at least 6, 8, 10, 12, or 14 cSt; additionally or alternatively, the maximum kinematic viscosity at 100° C. of the propylene oligomer or the heavy propylene oligomer can be 200, 175, 150, 125, 100, 80, 60, or 50 cSt. Generally, the kinematic viscosity at 100° C. of the propylene oligomer or the heavy propylene oligomer can be in a range from any minimum kinematic viscosity disclosed herein to any maximum kinematic viscosity disclosed herein. Therefore, suitable non-limiting ranges for the kinematic viscosity at 100° C. of the propylene oligomer or the heavy propylene oligomer can include the following ranges: from 6 to 200 cSt, from 8 to 150 cSt, from 10 to 150 cSt, from 10 to 100 cSt, from 12 to 150 cSt, from 12 to 100 cSt, from 12 to 80 cSt, from 12 to 60 cSt, or from 14 to 50 cSt. Other appropriate ranges for the kinematic viscosity at 100° C. of the propylene oligomer or the heavy propylene oligomer are readily apparent from this disclosure. Generally, the viscosities of the propylene oligomer or the heavy propylene oligomer can be measured using ASTM D7042-04 or ASTM D445.

The flash point of the propylene oligomer or the heavy propylene oligomer often can fall within a range from 140 to 300° C. For instance, the flash point of the propylene oligomer or the heavy propylene oligomer can be at least 140, 160, 180, 200, or 220° C.; additionally or alternatively, the maximum flash point can be 300, 280, 260, 240, 220, or 200° C. Generally, the flash point of the propylene oligomer or the heavy propylene oligomer can be in a range from any minimum flash point temperature disclosed herein to any maximum flash point temperature disclosed herein. Therefore, suitable non-limiting ranges for the flash point of the propylene oligomer or the heavy propylene oligomer can include the following ranges: from 140 to 300° C., from 140 to 260° C., from 140 to 220° C., from 140 to 190° C., from 160 to 240° C., or from 160 to 200° C. Other appropriate ranges for the flash point of the propylene oligomer or the heavy propylene oligomer are readily apparent from this disclosure. Generally, the flash point of the propylene oligomer or the heavy propylene oligomer is the Cleveland open cup flash point and can be measured using ASTM D92-05.

All molecular weights (Mp is the peak molecular weight, Mn is the number-average molecular weight, Mw is the weight-average molecular weight, and Mz is the z-average molecular weight) relating to the propylene oligomers disclosed herein were determined using the GPC procedure described herein using the molecular weight standards described herein. Due to limitations in the utilized GPC procedure and equipment, materials with molecular weights under about 125-150 g/mol may not be fully represented in the molecular weight distribution. For example, some $C_9$'s may be excluded from the molecular weight distribution because their boiling points were similar to that of sample preparation temperatures.

In an embodiment, the propylene oligomer or the heavy propylene oligomer can have a Mn in a range from 250 to 10,000 g/mol. For instance, the Mn of the propylene oligomer or the heavy propylene oligomer can be at least 250, 325, 400, 500, 600, 650, 700, or 750 g/mol; additionally or alternatively, the maximum Mn can be 10,000, 7500, 6000, 5000, 4000, 3000, 2500, or 2000 g/mol. Generally, the Mn of the propylene oligomer or the heavy propylene oligomer can be in a range from any minimum Mn disclosed herein to any maximum Mn disclosed herein. Therefore, suitable non-limiting ranges for the Mn of the propylene oligomer or the heavy propylene oligomer can include the following ranges: from 250 to 5000 g/mol, from 400 to 7500 g/mol, from 500 to 5000 g/mol, from 500 to 4000 g/mol, from 500 to 2500 g/mol, from 600 to 2500 g/mol, or from 750 to 2500 g/mol. Other appropriate ranges for the Mn of the propylene oligomer or the heavy propylene oligomer are readily apparent from this disclosure.

While not being limited thereto, the propylene oligomer or the heavy propylene oligomer often can have a Mw in a range from 500 to 10,000 g/mol. For instance, the Mw of the propylene oligomer or the heavy propylene oligomer can be at least 500, 750, 1000, 1250, or 1500 g/mol; additionally or alternatively, the maximum Mw can be 10,000, 9000, 7000, 5000, 4000, or 3000 g/mol. Generally, the Mw of the propylene oligomer or the heavy propylene oligomer can be in a range from any minimum Mw disclosed herein to any maximum Mw disclosed herein. Therefore, suitable non-limiting ranges for the Mw of the propylene oligomer or the heavy propylene oligomer can include the following ranges: from 500 to 10,000 g/mol, from 750 to 9000 g/mol, from 750 to 7000 g/mol, from 1000 to 5000 g/mol, from 500 to 4000 g/mol, from 500 to 3000 g/mol, from 1000 to 5000 g/mol, or from 1500 to 5000 g/mol. Other appropriate ranges for the Mw of the propylene oligomer or the heavy propylene oligomer are readily apparent from this disclosure.

The ratio of Mw/Mn, often referred to as the polydispersity index, of the propylene oligomer or the heavy propylene oligomer typically can range from 1.6 to 5. For instance, the Mw/Mn of the propylene oligomer can be at least 1.6, 1.7, 1.8, 1.9, or 2; additionally or alternatively, the maximum Mw/Mn can be 5, 4.5, 4, or 3.5. Generally, the Mw/Mn of the propylene oligomer or the heavy propylene oligomer can be in a range from any minimum Mw/Mn disclosed herein to any maximum Mw/Mn disclosed herein. Therefore, suitable non-limiting ranges for the Mw/Mn of the propylene oligomer or the heavy propylene oligomer can include the following ranges: from 1.6 to 5, from 1.8 to 5, from 1.8 to 4.5, from 1.9 to 4, or from 2 to 4. Other appropriate ranges for the Mw/Mn of the propylene oligomer or the heavy propylene oligomer are readily apparent from this disclosure.

The ratio of Mz/Mw of the propylene oligomer typically can range from 1.9 to 8. For instance, the Mz/Mw of the propylene oligomer or the heavy propylene oligomer can be at least 1.9, 2, or 2.2; additionally or alternatively, the maximum Mz/Mw can be 8, 6, 5, or 3. Generally, the Mz/Mw of the propylene oligomer or the heavy propylene oligomer can be in a range from any minimum Mz/Mw disclosed herein to any maximum Mz/Mw disclosed herein. Therefore, suitable non-limiting ranges for the Mz/Mw of the propylene oligomer or the heavy propylene oligomer can include the following ranges: from 1.9 to 8, from 1.9 to 6, from 1.9 to 5, from 1.9 to 3, from 2 to 8, from 2 to 6, from 2.2 to 8, or from 2.2 to 5. Other appropriate ranges for the Mz/Mw of the propylene oligomer or the heavy propylene oligomer are readily apparent from this disclosure.

The tacticity (e.g., the atactic content) of the propylene oligomer or the heavy propylene oligomer can be quantified by the mr triad content, and the mr triad content can fall within a range from 40 to 50 mol %. For instance, the mr triad content of the propylene oligomer or the heavy propylene oligomer can be at least 40, 41, 42, 43, 44, or 45%; additionally or alternatively, the maximum mr triad content can be 50, 49, 48, or 47%. Generally, the mr triad content of the propylene oligomer or the heavy propylene oligomer can be in a range from any minimum mr triad content disclosed herein to any maximum mr triad content disclosed herein. Therefore, suitable non-limiting ranges for the mr triad content of the propylene oligomer or the heavy propylene oligomer can include the following ranges: from 40 to 50%, from 41 to 49%, from 42 to 50%, from 42 to 49%, from 43 to 48%, from 44 to 49%, or from 45 to 50%. Other appropriate ranges for the mr triad content of the propylene oligomer are readily apparent from this disclosure.

In embodiments of this invention, the repeating units of the propylene oligomer or the heavy propylene oligomer can be substantially all propylene units. That is, the repeating units of the propylene oligomer or the heavy propylene oligomer can contain at least 98 mol % propylene units, and in some embodiments, at least 98.5 mol % propylene units, at least 99 mol % propylene units, at least 99.25 mol % propylene units, at least 99.5 mol % propylene units, or at least 99.75 mol % propylene units.

The propylene oligomer can be a liquid propylene oligomer in particular embodiments of this invention. Thus, the propylene oligomer can be a liquid (not a solid or gas) at standard temperature (25° C.) and pressure (1 atm).

In some embodiments, the propylene oligomer or heavy oligomer product can be hydrogenated to form a hydrogenated propylene oligomer or hydrogenated heavy oligomer product. Suitable hydrogenation procedures and associated metal catalysts (e.g., platinum, rhenium, palladium, nickel, etc.) are well known to those of skill in the art. The hydrogenated propylene oligomer or hydrogenated propylene oligomer can have any of the propylene oligomer characteristics or properties disclosed herein (e.g., viscosity index, viscosity, pour point, Mn, Mz/Mw, etc.), and in any combination.

In an embodiment, the hydrogenated propylene oligomer or hydrogenated heavy propylene oligomer can have any bromine number or bromine index described herein. In some embodiments, the hydrogenated propylene oligomer or hydrogenated heavy propylene oligomer described herein can have a maximum bromine number of 2, 1.8, 1.6, 1.4, 1.2, or 1 grams of bromine per 100 grams of sample (g Br/100 g). In other embodiments, the hydrogenated propylene oligomer or hydrogenated heavy propylene oligomer described herein can have a maximum bromine index of 1000, 800, 600, or 500 milligrams of bromine per 100 grams of sample (mg Br/100 g). Generally, the bromine number can be determined by ASTM D1159-09, while the bromine index can be determined by ASTM D2710-09.

Oligomerization Processes

Embodiments of this invention are directed to propylene oligomerization processes, the production of an oligomer product, and the formation and recovery of a propylene oligomer, whose typical properties are disclosed herein. A representative process can comprise (or consist essentially of, or consist of) contacting an olefin feedstock comprising propylene with a catalyst system comprising (i) a metallocene compound, (ii) a chemically-treated solid oxide, and (iii) an optional co-catalyst, to form an oligomer product under oligomerization conditions.

Generally, the features of the processes (e.g., the olefin feedstock, the catalyst system, the metallocene compound, the chemically-treated solid oxide, the co-catalyst, the materials comprising and/or features of the oligomer product, the oligomerization conditions under which the oligomer product is formed, among others) are independently described herein, and these features can be combined in any combination to further describe the disclosed processes. Moreover, additional process steps can be performed before, during, and/or after any of the steps of any of the processes disclosed herein, unless stated otherwise.

The olefin feedstock comprising propylene can come from many different sources and have a wide range of compositional attributes. In one embodiment, for example, a composition comprising the olefin feedstock can comprise (a) at least 66, 70, 74, 76, 78, 80, 82, or 84 mol % propylene, (b) less than 34, 30, 26, 24, 22, 18, or 16 mol % $C_1$ to $C_{4+}$ paraffins, (c) less than 4, 3, or 2 mol % $C_2$ and/or $C_{4+}$ olefins, or (d) any combination of these materials and respective amounts. In another embodiment, a composition comprising the olefin feedstock can be refinery grade propylene. In another embodiment, a composition comprising the olefin feedstock can comprise (a) at least 90, 91, 92, 93, or 94 mol % propylene, (b) less than 10, 9, 8, 7, or 6 mol % $C_1$ to $C_{4+}$ paraffins, (c) less than 2, 1, 0.5, 0.25, or 0.1 mol % $C_2$ and/or $C_{4+}$ olefins, or (d) any combination of these materials and respective amounts. In another embodiment, a composition comprising the olefin feedstock can be chemical grade propylene. In yet another embodiment, a composition comprising the olefin feedstock can comprise (a) at least 98, 98.5, 99, 99.25 or 99.5 mol % propylene, (b) less than 2, 1.5, 1, 0.75, or 0.5 mol % $C_1$ to $C_{4+}$ paraffins, (c) less than 0.5, 0.25, 0.1, 0.075, or 0.05 mol % $C_2$ and/or $C_{4+}$ olefins, or (d) any combination of these materials and respective amounts. In still another embodiment, a composition comprising the olefin feedstock can be polymer grade propylene.

The oligomerization conditions can comprise any suitable oligomerization temperature. For example, the oligomerization temperature can be in a range from 0° C. to 165° C. In some embodiments, the oligomerization temperature can be in a range from 20° C. to 160° C., from 40° C. to 160° C., or from 40° C. to 150° C., while in other embodiments, the oligomerization temperature can be in a range from 50° C. to 150° C., from 50° C. to 140° C., or from 50° C. to 130° C. Yet, in further embodiments, the oligomerization temperature can be in a range from 60° C. to 130° C., from 60° C. to 120° C., or from 60° C. to 90° C. Other appropriate oligomerization temperatures and temperature ranges are readily apparent from this disclosure.

The oligomerization conditions can comprise any suitable reaction pressure (or propylene partial pressure). For example, the reaction pressure (or propylene partial pressure) under which the oligomerization is conducted can be in a range from 50 psig (344 kPa) to 4,000 psig (27.6 MPa), from 100 psig (689 KPa) to 3,000 psig (20.9 MPa), or from 150 psig (1.0 MPa) to 2500 psig (17.2 MPa). In some embodiments, the reaction pressure (or propylene partial pressure) can be in a range from 200 psig (1.4 MPa) to 2500 psig (17.2 MPa), from 200 psig (1.4 MPa) to 2,000 psig (13.8 MPa), from 250 psig (1.4 MPa) to 2,000 psig (1.7 MPa), or from 250 psig (1.5 MPa) to 1,500 psig (10.3 MPa). Other appropriate reaction pressures (or propylene partial pressures) are readily apparent from this disclosure.

In some embodiments, the oligomer product can be formed in the substantial absence of hydrogen. In these embodiments, no hydrogen is added to the oligomerization reaction system. As one of ordinary skill in the art would recognize, hydrogen can be generated in-situ by metallocene catalyst systems in various olefin oligomerization processes, and the amount generated can vary depending upon the specific catalyst system and metallocene compound employed, the type of oligomerization process used, the oligomerization reaction conditions utilized, and so forth.

In other embodiments, it may be desirable to conduct the oligomerization process in the presence of a certain amount of added hydrogen, for instance, to reduce molecular weight, to reduce viscosity, etc. Accordingly, in these embodiments, the oligomer product can be formed in the presence of hydrogen, i.e., the olefin feedstock (containing propylene), the catalyst system, and hydrogen can be contacted to form the oligomer product under oligomerization conditions. For instance, the oligomer product can be formed at a hydrogen partial pressure of at least 1 psig (6.9 kPa), 5 psig (34 kPa), 10 psig (69 kPa), 25 psig (172 kPa), or 50 psig (345 kPa); additionally or alternatively, the oligomer product can be formed at a maximum hydrogen partial pressure of 2000 psig (13.8 MPa), 1750 psig (12.1 MPa), 1500 psig (10.3 MPa), 1250 psig (8.6 MPa), 1000 psig (6.9 MPa), 750 psig (5.2 MPa), 500 psig (3.4 MPa), or 400 psig (2.8 MPa). Generally, the hydrogen partial pressure can range from any minimum hydrogen partial pressure disclosed herein to any maximum hydrogen partial pressure disclosed herein. Therefore, suitable non-limiting ranges for the hydrogen partial pressure can include the following ranges: from 1 psig (6.9 kPa) to 2000 psig (13.8 MPa), from 1 psig (6.9 kPa) to 1750 psig (12.1 MPa), from 5 psig (34 kPa) to 1500 psig (10.3 MPa), from 5 psig (34 kPa) to 1250 psig (8.6 MPa), from 10 psig (69 kPa) to 1000 psig (6.9 MPa), from 10 psig (69 kPa) to 750 psig (5.2 MPa), from 10 psig (69 kPa) to 500 psig (3.5 MPa), from 25 psig (172 kPa) to 750 psig (5.2 MPa), from 25 psig (172 kPa) to 500 psig (3.4 MPa), or from 50 psig (345 kPa) to 500 psig (3.4 MPa). Other appropriate hydrogen partial pressures are readily apparent from this disclosure.

In a particular embodiment, and unexpectedly, the catalyst system (and related oligomerization process) can be very responsive to hydrogen addition. For instance, the decrease in the Mn of the oligomer product produced by the process in the presence of hydrogen can be greater than the decrease in the Mn of an oligomer product produced by a catalyst system containing an aluminoxane activator (e.g., MAO), instead of the chemically-treated solid oxide, under the same oligomerization conditions. The same oligomerization conditions means that all components (other than chemically-treated solid oxide and aluminoxane) used to prepare the catalyst systems are held constant (e.g., same amount/type of metallocene compound, same amount/type of co-catalyst, etc.) and all oligomerization conditions are held constant (e.g., same temperature, same pressure, same reactant ratios, etc.). Hence, the only difference is the use of the chemically-treated solid oxide versus the use of the aluminoxane. While not wishing to be bound by the following theory, it is believed that the improved hydrogen response of the catalyst system containing a chemically-treated solid oxide (and related process) can result in the production of lower molecular weight and lower viscosity oligomers without the excessive use of hydrogen. Moreover, the use of hydrogen, unexpectedly, can increase catalyst activity and oligomer productivity with certain catalyst systems disclosed herein.

Any suitable reactor or vessel within an oligomerization reaction system can be used to form the oligomer product, non-limiting examples of which can include a fixed bed reactor, a stirred tank reactor, and a plug flow reactor, including more than one reactor in series or in parallel, and including any combination of reactor types and arrangements.

In the processes described herein, the catalyst system can be deactivated. Deactivating the catalyst system can comprise contacting the oligomer product with a suitable catalyst system deactivating agent, or subjecting the oligomer product to suitable process steps to deactivate the catalyst system, or a combination of both. The catalyst system deactivating agent can comprise (or consist essentially of, or consist of) water, an alcohol compound, an amine compound, or any combination thereof; alternatively, water; alternatively, an alcohol compound; or alternatively, an amine compound. In an embodiment, the alcohol compound can be a monoalcohol compound, a diol compound, a polyol compound, or any combination thereof. In some embodiments, the alcohol compound can comprise, consist essentially of, or consist of, a $C_1$ to $C_{20}$ mono alcohol. In some embodiments, the alcohol compound can comprise, consist essentially of, or consist of, methanol, ethanol, a propanol, a butanol, a pentanol, a hexanol, a heptanol, an octanol, a nonanol, a decanol, an undecanol, or mixtures thereof. In some embodiments, the alcohol compound can comprise, consist essentially of, or consist of, methanol, ethanol, 1-propanol, 2-propanol, 1-butanol, 2-butanol, iso-butanol, sec-butanol, t-butanol, 1-hexanol, 2-hexanol, 3-hexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-decanol, 2-decanol, 3-decanol, 4-decanol, 5-decanol, 1-undecanol, 2-undecanol, 7-methyl-2-decanol, a 1-docecanol, a 2-dodecanol, 2-ethyl-1-decanol, and mixtures thereof.

Additionally or alternatively, the catalyst system can be deactivated by contact with an aqueous solution (e.g., an aqueous Group 1 metal hydroxide solution or an aqueous mineral acid solution). Such deactivation processes to deactivate the catalyst system can also potentially remove a portion, or substantially all, of the metal catalyst system components from the oligomer product.

In the processes described herein, the processes can further comprise a step of separating unreacted monomer (e.g., propylene) and the oligomer product from the catalyst system or deactivated catalyst system. Various suitable separations steps can be employed, as would be recognized by those of skill in the art. In an embodiment, and not limited thereto, a filtration step can be used.

In some embodiments, a heavy propylene oligomer can be isolated. One such technique for isolating the heavy propylene oligomer can comprise a step of removing unreacted propylene and at least a portion of the light propylene oligomers (e.g., $C_6$-$C_{12}$, etc.) from the oligomer product. In these and other embodiments, various suitable separation or isolation steps can be employed, as would be recognized by those of skill in the art. In an embodiment, such separation or isolation steps can include one or more batch or continuous flash processes, one or more batch or continuous distillation processes, and combinations thereof. In another embodiment, a flash process at atmospheric or any suitable sub-atmospheric pressure can be utilized, while in yet another embodiment, a distillation process at atmospheric or any suitable sub-atmospheric pressure can be utilized. Suitable sub-atmospheric pressures can include, but are not limited to, less than 100 torr (13.3 kPa), less than 50 (6.67 kPa) torr, less than 10 torr (1.33 kPa), or less than 5 torr (0.67 kPa). The conditions that are used to isolate the heavy propylene oligomer can be varied based on the desired molecular weight properties (e.g., Mn, Mz/Mw, etc.), the desired viscosity properties (e.g., viscosity index, pour point, viscosity at 40° C., viscosity at 100° C., etc.), and the identity and/or quantity of the particular oligomer to be removed to isolate the heavy propylene oligomer. As a representative example, the separation conditions can be selected to produce a heavy propylene oligomer having a specified flash point. The flash point of the heavy propylene oligomer often can fall within a range from 140 to 300° C. For instance, the flash point of the heavy propylene oligomer can be at least 140, 160, 180, 200, or 220° C.; additionally or alternatively, the maximum flash point can be 300, 280, 260, 240, 220, or 200° C. Generally, the flash point of the heavy propylene oligomer can be in a range from any minimum flash point temperature disclosed herein to any maximum flash point temperature disclosed herein. Therefore, suitable non-limiting ranges for the flash point of the heavy propylene oligomer can include the following ranges: from 140 to 300° C., from 140 to 260° C., from 140 to 220° C., from 140 to 190° C., from 160 to 240° C., or from 160 to 200° C. Other appropriate ranges for the flash point of the heavy propylene oligomer are readily apparent from this disclosure.

In some embodiments, the oligomer product can have any of the properties of the propylene oligomer disclosed herein, while in other embodiments, the heavy propylene oligomer can have any of the properties of the propylene oligomer disclosed herein, and in any combination. Thus, the oligomer product (or heavy propylene oligomer) can be characterized by a Mn in a range from 250 to 10,000 g/mol, a viscosity index of at least 85, and a pour point in a range from −5 to −60° C. Additionally or alternatively, the oligomer product (or heavy propylene oligomer) can be characterized by a Mn in a range from 250 to 10,000 g/mol, a ratio of Mz/Mw in a range from 1.9 to 8, and a viscosity index of at least 85. In an embodiment, the heavy propylene oligomer can be comprised of substantially all propylene units, i.e., containing at least 98 mol % propylene units, and in some embodiments, at least 98.5 mol % propylene units, at least 99 mol % propylene units, at least 99.25 mol % propylene units, at least 99.5 mol % propylene units, or at least 99.75 mol % propylene units.

In an embodiment, the processes described herein can further comprise a step of hydrogenating the oligomer product (or the heavy propylene oligomer). Any suitable hydrogenation process and associated catalyst can be used, and such hydrogenation processes and catalysts (e.g., platinum, rhenium, palladium, nickel, etc.) are well known to those of skill in the art. Generally, the oligomer product or the heavy propylene oligomer can be hydrogenated to provide a hydrogenated oligomer product or hydrogenated heavy propylene oligomer having the desired degree of saturation (which can be quantified as any bromine number or bromine index described herein). In an embodiment, the oligomer product or the heavy propylene oligomer can be hydrogenated to provide a hydrogenated oligomer product or hydrogenated heavy propylene oligomer having any bromine number or bromine index described herein. The hydrogenated oligomer product (or hydrogenated heavy propylene oligomer) can have any of the propylene oligomer (or hydrogenated propylene oligomer) characteristics or properties disclosed herein (e.g., viscosity index, pour point, Mn, Mz/Mw, etc.), and in any combination. Embodiments of the present invention also are directed to and encompass any heavy propylene oligomer or hydrogenated heavy propylene oligomer produced by any of the processes disclosed herein.

Catalyst Systems

In the processes disclosed herein, an olefin feedstock comprising propylene can be contacted with a catalyst system comprising (i) a metallocene compound, (ii) a chemically-treated solid oxide, and (iii) an optional co-catalyst, thereby forming an oligomer product. Any metallocene-based catalyst system suitable for the oligomerization of propylene, and containing the aforementioned components, can be employed in this invention.

The metallocene compound can comprise, for example, a transition metal (one or more than one) from Groups IIIB-XB of the Periodic Table of the Elements. In one embodiment, the metallocene compound can comprise a Group III, IV, V, or VI transition metal, or a combination of two or more transition metals. The metallocene compound can comprise chromium, titanium, zirconium, hafnium, vanadium, or a combination thereof, in some embodiments, or can comprise chromium, titanium, zirconium, hafnium, or a combination thereof, in other embodiments. Accordingly, the metallocene compound can comprise chromium, or titanium, or zirconium, or hafnium, either singly or in combination. In some embodiments, the metallocene compound can comprise zirconium. Moreover, catalyst systems comprising two or more metallocene compounds, wherein each metallocene compound independently can comprise chromium, titanium, zirconium, hafnium, vanadium, or a combination thereof, are contemplated and encompassed herein.

The metallocene compound can comprise a bridged metallocene compound. In one embodiment, the metallocene compound can comprise a bridged zirconium or hafnium based metallocene compound. In another embodiment, the metallocene compound can comprise a bridged zirconium or hafnium based metallocene compound with a carbon bridging atom or a silicon bridging atom. In yet another embodiment, the metallocene compound can comprise a bridged zirconium based metallocene with a cyclopentadienyl group and a carbon bridging atom or a silicon bridging atom. In still another embodiment, the metallocene compound can comprise a bridged zirconium based metallocene with two cyclopentadienyl groups and a carbon bridging atom or a silicon bridging atom.

In these and other embodiments, the bridged metallocene compound can contain an alkyl substituent (e.g., n-butyl, n-propyl) on the bridging atom. Additionally or alternatively, the bridged metallocene compound can contain an alkyl substituent, for example, on the bridging atom and/or on a cyclopentadienyl group.

The metallocene compound is not limited solely to the bridged metallocene compounds such as described above. Other suitable bridged metallocene compounds are disclosed in U.S. Pat. Nos. 7,026,494, 7,041,617, 7,226,886, 7,312,283, 7,517,939, and 7,619,047.

In certain embodiments of this invention, the catalyst system can contain a metallocene compound, and the metallocene compound can comprise an unbridged metallocene compound. In one embodiment, the metallocene compound can comprise an unbridged zirconium or hafnium based metallocene compound and/or an unbridged zirconium and/or hafnium based dinuclear metallocene compound. In another embodiment, the metallocene compound can comprise an unbridged zirconium or hafnium based metallocene compound containing two cyclopentadienyl groups, two indenyl groups, or a cyclopentadienyl and an indenyl group. In another embodiment, the metallocene compound can comprise an unbridged zirconium or hafnium based metallocene compound containing two cyclopentadienyl groups. In another embodiment, the metallocene compound can comprise an unbridged zirconium based metallocene compound containing two cyclopentadienyl groups. In another embodiment, the metallocene compound can comprise an unbridged zirconium or hafnium based metallocene compound containing two indenyl groups. In another embodiment, the metallocene compound can comprise an unbridged zirconium or hafnium based metallocene compound containing a cyclopentadienyl and an indenyl group. In yet another embodiment, the metallocene compound can comprise an unbridged zirconium based metallocene compound containing a cyclopentadienyl and an indenyl group. In still another embodiment, the metallocene compound can comprise an unbridged zirconium based metallocene compound containing a cyclopentadienyl group and an indenyl group with an alkenyl substituent.

In these and other embodiments, the unbridged metallocene compound can contain an alkyl substituent (e.g., n-butyl, n-propyl) on one or both cyclopentadienyl-type groups (e.g., a cyclopentadienyl group, an indenyl group). Accordingly, the metallocene compound can contain an alkyl-substituted cyclopentadienyl group.

Illustrative and non-limiting examples of bridged and unbridged metallocene compounds that are suitable for use as metallocene compounds described herein can include the following compounds (Ph=phenyl):

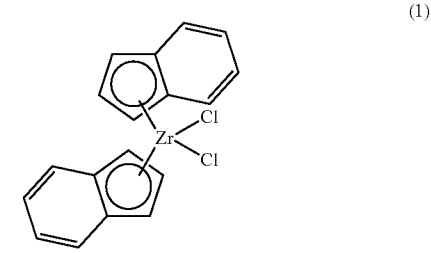

(1)

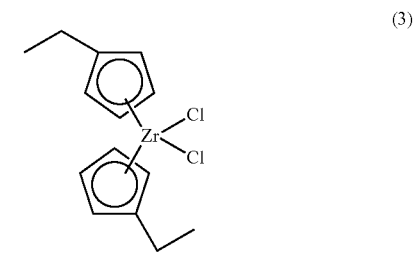

(3)

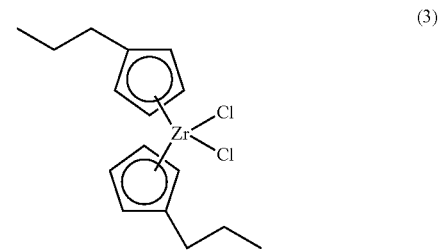

(3)

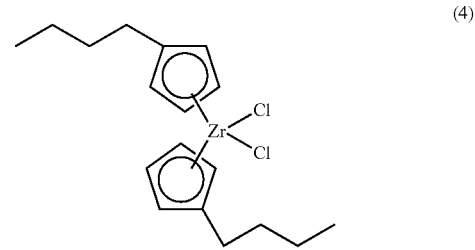

(4)

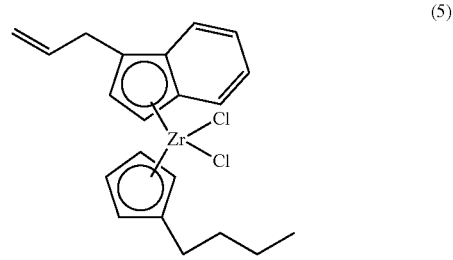

(5)

-continued (6) 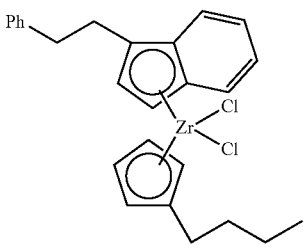

(7) 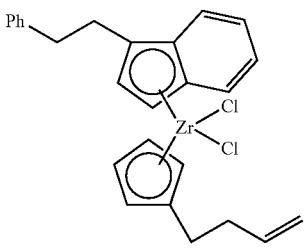

(8) 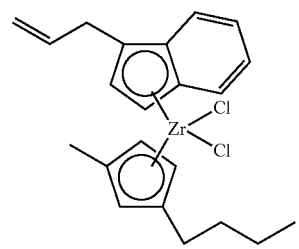

(9) 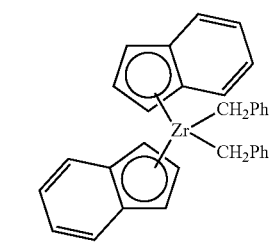

(10) 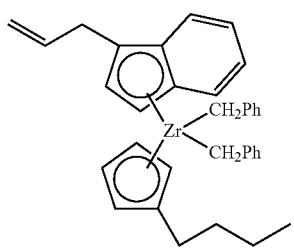

(11) 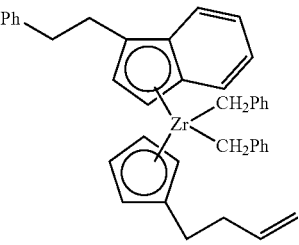

-continued

(12) 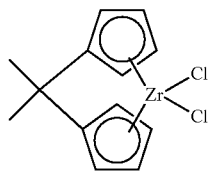

(13) 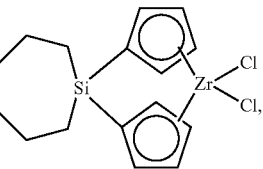

as well as combinations thereof.

The metallocene compound is not limited solely to bridged and unbridged metallocene compounds such as described above, or to suitable unbridged metallocene compounds disclosed in U.S. Pat. Nos. 7,199,073, 7,226,886, 7,312,283, and 7,619,047. For example, the metallocene compound can comprise an unbridged dinuclear metallocene compound, such as those described in U.S. Pat. Nos. 7,919,639 and 8,080,681. Illustrative and non-limiting examples of dinuclear metallocene compounds suitable for use in the present invention can include the following compounds:

(14) 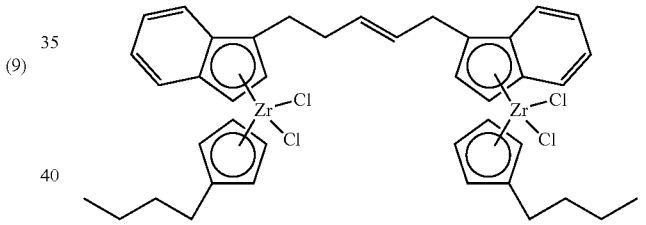

(15) 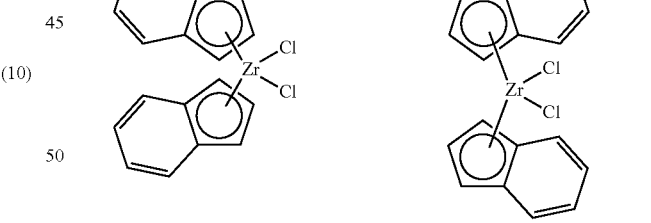

as well as combinations thereof.

The catalyst systems of the present invention, in addition to a metallocene compound (one or more), can contain a chemically-treated solid oxide and, optionally, a co-catalyst. In one embodiment, the chemically-treated solid oxide can comprise a solid oxide treated with an electron-withdrawing anion. Alternatively, in another embodiment, the chemically-treated solid oxide can comprise a solid oxide treated with an electron-withdrawing anion, the solid oxide containing a Lewis-acidic metal ion. Non-limiting examples of suitable chemically-treated solid oxides are disclosed in, for instance, U.S. Pat. Nos. 7,294,599, 7,601,665, 7,884,163, 8,309,485, 8,623,973, 8,703,886, and 9,023,959.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form a chemically-treated solid oxide, either singly or in combination, can include, but are not limited to, silica-alumina, silica-titania, silica-zirconia, alumina-titania, alumina-zirconia, zinc-aluminate, alumina-boria, silica-boria, aluminophosphate-silica, and titania-zirconia. The solid oxide used herein also can encompass oxide materials such as silica-coated alumina, as described in U.S. Pat. No. 7,884,163.

Accordingly, in one embodiment, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another embodiment, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. In another embodiment, the solid oxide can comprise silica, alumina, titania, zirconia, magnesia, boria, zinc oxide, any mixed oxide thereof, or any combination thereof. In yet another embodiment, the solid oxide can comprise silica-alumina, silica-coated alumina, silica-titania, silica-zirconia, alumina-boria, or any combination thereof. In still another embodiment, the solid oxide can comprise silica, alumina, silica-alumina, silica-coated alumina, or any mixture thereof; alternatively, silica; alternatively, alumina; alternatively, silica-alumina; or alternatively, silica-coated alumina.

The silica-alumina or silica-coated alumina solid oxide materials which can be used can have a silica content from 5 to 95% by weight. In one embodiment, the silica content of these solid oxides can be from 10 to 80%, or from 20% to 70%, silica by weight. In another embodiment, such materials can have silica contents ranging from 15% to 60%, or from 25% to 50%, silica by weight. The solid oxides contemplated herein can have any suitable surface area, pore volume, and particle size, as would be recognized by those of skill in the art.

The electron-withdrawing component used to treat the solid oxide can be any component that increases the Lewis or Brønsted acidity of the solid oxide upon treatment (as compared to the solid oxide that is not treated with at least one electron-withdrawing anion). According to one embodiment, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, and molybdate, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, or any combination thereof, in some embodiments provided herein. In other embodiments, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, or combinations thereof. Yet, in other embodiments, the electron-withdrawing anion can comprise fluoride and/or sulfate.

The chemically-treated solid oxide generally can contain from 1 to 25 wt. % of the electron-withdrawing anion, based on the weight of the chemically-treated solid oxide. In particular embodiments provided herein, the chemically-treated solid oxide can contain from 1 to 20 wt. %, from 2 to 20 wt. %, from 3 to 20 wt. %, from 2 to 15 wt. %, from 3 to 15 wt. %, from 3 to 12 wt. %, or from 4 to 10 wt. %, of the electron-withdrawing anion, based on the total weight of the chemically-treated solid oxide.

In an embodiment, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, or phosphated silica-coated alumina, as well as any mixture or combination thereof. In another embodiment, the chemically-treated solid oxide employed in the catalyst systems described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, fluorided-chlorided silica-coated alumina, or sulfated silica-coated alumina, as well as combinations thereof. In yet another embodiment, the chemically-treated solid oxide can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some embodiments, the chemically-treated solid oxide can comprise a fluorided solid oxide, while in other embodiments, the chemically-treated solid oxide can comprise a sulfated solid oxide.

Various processes can be used to form chemically-treated solid oxides useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485. Other suitable processes and procedures for preparing chemically-treated solid oxides (e.g., fluorided solid oxides, sulfated solid oxides, etc.) are well known to those of skill in the art.

In certain embodiments of this invention, the catalyst system contains a co-catalyst, such as a metal hydrocarbyl compound, examples of which include non-halide metal hydrocarbyl compounds, metal hydrocarbyl halide compounds, non-halide metal alkyl compounds, metal alkyl halide compounds, and so forth. The hydrocarbyl group (or alkyl group) can be any hydrocarbyl (or alkyl) group disclosed herein. Moreover, in some embodiments, the metal of the metal hydrocarbyl can be a group 1, 2, 11, 12, 13, or 14 metal; alternatively, a group 13 or 14 metal; or alternatively, a group 13 metal. Hence, in some embodiments, the metal of the metal hydrocarbyl (non-halide metal hydrocarbyl or metal hydrocarbyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some embodiments, the metal hydrocarbyl or metal alkyl, with or without a halide, can comprise a lithium hydrocarbyl or alkyl, a magnesium hydrocarbyl or alkyl, a boron hydrocarbyl or alkyl, a zinc hydrocarbyl or alkyl, or an aluminum hydrocarbyl or alkyl.

In an embodiment, each hydrocarbyl group of the metal hydrocarbyl compound or metal hydrocarbyl halide compound independently can be a $C_1$ to $C_{20}$ hydrocarbyl group; alternatively, a $C_1$ to $C_{10}$ hydrocarbyl group; or alternatively, a $C_1$ to $C_6$ hydrocarbyl group. In an embodiment, each alkyl group of the metal alkyl hydrocarbyl compound or the metal alkyl halide compound independently can be a $C_1$ to $C_{20}$ alkyl group; alternatively, a $C_1$ to $C_{10}$ alkyl group; or alternatively, a $C_1$ to $C_6$ alkyl group. In an embodiment, each alkyl group(s) of any metal alkyl compound or metal alkyl halide compound independently can be a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, each alkyl group(s) of any metal alkyl compound or metal alkyl halide compound independently can be independently can be, comprise, or consist essentially of, a methyl group, an ethyl group, an n-propyl group, an n-butyl group, an iso-butyl group, an n-hexyl group, or an n-octyl group; or alternatively, a methyl group, an ethyl group, an n-butyl group, or an iso-butyl group.

In particular embodiments directed to catalyst systems containing a co-catalyst (i.e., the catalyst system contains a chemically-treated solid oxide), the co-catalyst can comprise an aluminoxane compound, an organoboron or organoborate compound, an ionizing ionic compound, an organoaluminum compound, an organozinc compound, an organomagnesium compound, or an organolithium compound, and this includes any combinations of these materials. In one embodiment, the co-catalyst can comprise an organoaluminum compound. In another embodiment, the co-catalyst can comprise an aluminoxane compound, an organoboron or organoborate compound, an ionizing ionic compound, an organozinc compound, an organomagnesium compound, an organolithium compound, or any combination thereof. In yet another embodiment, the co-catalyst can comprise an organoaluminum compound, an organozinc compound, an organomagnesium compound, an organolithium compound, or any combination thereof. In still another embodiment, the co-catalyst can comprise an aluminoxane compound; alternatively, an organoboron or organoborate compound; alternatively, an ionizing ionic compound; alternatively, an organozinc compound; alternatively, an organomagnesium compound; or alternatively, an organolithium compound.

Specific non-limiting examples of suitable organoaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, and diethylaluminum chloride, or combinations thereof. Representative and non-limiting examples of aluminoxanes include methylaluminoxane, modified methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentyl-aluminoxane, and neopentylaluminoxane, or any combination thereof. Representative and non-limiting examples of organoboron/organoborate compounds include N,N-dimethylanilinium tetrakis-(pentafluorophenyl)borate, triphenylcarbenium tetrakis(pentafluorophenyl)borate, lithium tetrakis-(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, tris(pentafluorophenyl)boron, and tris[3,5-bis(trifluoromethyl)phenyl]boron, or mixtures thereof.

Examples of ionizing ionic compounds can include, but are not limited to, the following compounds: tri(n-butyl)ammonium tetrakis(p-tolyl)borate, tri(n-butyl) ammonium tetrakis(m-tolyl)borate, tri(n-butyl) ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoro-methyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoromethyl)phenyl]borate, triphenylcarbenium tetrakis(pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis(pentafluorophenyl) borate, lithium tetrakis(pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis(pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis(pentafluorophenyl)aluminate, sodium tetraphenylaluminate, sodium tetrakis(p-tolyl)-aluminate, sodium tetrakis(m-tolyl) aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis(3,5-dimethylphenyl)aluminate, and potassium tetrafluoroaluminate, or combinations thereof.

Exemplary organozinc compounds which can be used as co-catalysts can include, but are not limited to, dimethylzinc, diethylzinc, dipropylzinc, dibutylzinc, dineopentylzinc, di(trimethylsilyl)zinc, di(triethylsilyl)zinc, di(triisoproplysilyl)zinc, di(triphenylsilyl)zinc, di(allyldimethylsilyl)zinc, and di(trimethylsilylmethyl)zinc, or combinations thereof.

Similarly, exemplary organomagnesium compounds can include, but are not limited to, dimethylmagnesium, diethylmagnesium, dipropylmagnesium, dibutylmagnesium, dineopentylmagnesium, di(trimethylsilylmethyl)magnesium, methylmagnesium chloride, ethylmagnesium chloride, propylmagnesium chloride, butylmagnesium chloride, neopentylmagnesium chloride, trimethylsilylmethylmagnesium chloride, methylmagnesium bromide, ethylmagnesium bromide, propylmagnesium bromide, butylmagnesium bromide, neopentylmagnesium bromide, trimethylsilylmethylmagnesium bromide, methylmagnesium iodide, ethylmagnesium iodide, propylmagnesium iodide, butylmagnesium iodide, neopentylmagnesium iodide, trimethylsilylmethylmagnesium iodide, methylmagnesium ethoxide, ethylmagnesium ethoxide, propylmagnesium ethoxide, butylmagnesium ethoxide, neopentylmagnesium ethoxide, trimethylsilylmethylmagnesium ethoxide, methylmagnesium propoxide, ethylmagnesium propoxide, propylmagnesium propoxide, butylmagnesium propoxide, neopentylmagnesium propoxide, trimethylsilylmethylmagnesium propoxide, methylmagnesium phenoxide, ethylmagnesium phenoxide, propylmagnesium phenoxide, butylmagnesium phenoxide, neopentylmagnesium phenoxide, and trimethylsilylmethylmagnesium phenoxide, or any combinations thereof.

Likewise, exemplary organolithium compounds can include, but are not limited to, methyllithium, ethyllithium, propyllithium, butyllithium (e.g., t-butyllithium), neopentyllithium, trimethylsilylmethyllithium, phenyllithium, tolyllithium, xylyllithium, benzyllithium, (dimethylphenyl)methyllithium, and allyllithium, or combinations thereof.

Co-catalysts that can be used in the catalyst systems of this invention are not limited to the co-catalysts described above. Other suitable co-catalysts are well known to those of skill in the art including, for example, those disclosed in U.S. Pat. Nos. 3,242,099, 4,794,096, 4,808,561, 5,576,259, 5,807,938, 5,919,983, 7,294,599 7,601,665, 7,884,163, 8,114,946, and 8,309,485.

In accordance with embodiments of this invention, a catalyst system is provided which comprises a metallocene compound, a chemically-treated solid oxide, and an organoaluminum compound. In some embodiments, this catalyst composition is substantially free of aluminoxanes, organoboron or organoborate compounds, ionizing ionic compounds, and/or other similar materials; alternatively, substantially free of aluminoxanes; alternatively, substantially free or organoboron or organoborate compounds; or alternatively, substantially free of ionizing ionic compounds. In these embodiments, the catalyst system can have catalyst activity, discussed herein, in the absence of aluminoxanes, organoboron or organoborate compounds, ionizing ionic compounds, and/or other similar materials. For example, a catalyst system of the present invention can consist essentially of a metallocene compound, a chemically-treated solid oxide, and an organoaluminum compound, wherein no other materials are present in the catalyst system which would increase/decrease the activity of the catalyst system by more than 10% from the catalyst activity of the catalyst system in the absence of said materials.

This invention further encompasses methods of making these catalyst systems, such as, for example, contacting the respective catalyst components in any order or sequence. In one embodiment, the catalyst system can be produced by a process comprising contacting the metallocene compound and the chemically-treated solid oxide, while in another embodiment, the catalyst system can be produced by a process comprising contacting, in any order, the metallocene compound, the chemically-treated solid oxide, and the co-catalyst (e.g., an organoaluminum compound, such as TEA or TIBA).

While not being limited thereto, the weight ratio of the chemically-treated solid oxide to the metallocene compound often can fall within a range from 50:1 to 1500:1. For instance, the weight ratio of the chemically-treated solid oxide to the metallocene compound can be at least 50:1, 60:1, 70:1 or 80:1; additionally or alternatively, the maximum weight ratio of the chemically-treated solid oxide to the metallocene compound can be 1500:1, 1000:1, 800:1, 600:1, or 500:1. Generally, the weight ratio of the chemically-treated solid oxide to the metallocene compound can be in a range from any minimum weight ratio disclosed herein to any maximum weight ratio disclosed herein. Therefore, suitable non-limiting ranges for the weight ratio of the chemically-treated solid oxide to the metallocene compound can include the following ranges: from 50:1 to 1500:1, from 50:1 to 1000:1, from 50:1 to 800:1, from 60:1 to 800:1, from 60:1 to 600:1, from 70:1 to 600:1, from 70:1 to 500:1, or from 80:1 to 500:1. Other appropriate ranges for the weight ratio of the chemically-treated solid oxide to the metallocene compound are readily apparent from this disclosure. If more than one metallocene compound and/or more than chemically-treated solid oxide is/are employed, this ratio is based on the total weights of the respective components.

The molar ratio of the co-catalyst (e.g., an organoaluminum compound) to the metallocene compound often ranges from 5:1 to 5000:1. For instance, the molar ratio of the co-catalyst to the metallocene compound can be at least 5:1, 10:1, 15:1 or 50:1; additionally or alternatively, the maximum molar ratio of the co-catalyst to the metallocene compound can be 5000:1, 2500:1, 1000:1, 250:1, or 150:1. Generally, the molar ratio of the co-catalyst to the metallocene compound can be in a range from any minimum molar ratio disclosed herein to any maximum molar ratio disclosed herein. Therefore, suitable non-limiting ranges for the molar ratio of the co-catalyst to the metallocene compound can include the following ranges: from 5:1 to 5000:1, from 5:1 to 1000:1, from 5:1 to 250:1, from 10:1 to 2500:1, from 10:1 to 1000:1, from 10:1 to 150:1, from 15:1 to 150:1, or from 50:1 to 1000:1. Other appropriate ranges for the molar ratio of the co-catalyst to the metallocene compound are readily apparent from this disclosure. If more than one metallocene compound and/or more than co-catalyst is/are employed, this ratio is based on the total moles of the respective components.

In accordance with the present invention, a process is provided that comprises contacting an olefin feedstock comprising (or consisting essentially of) propylene with a catalyst system comprising (or consisting essentially of) (i) a metallocene compound, (ii) a chemically-treated solid oxide, and (iii) an optional co-catalyst, thereby forming an oligomer product. While not being limited thereto, the molar ratio of propylene to the metallocene compound often ranges from $1 \times 10^3:1$ to $1 \times 10^9:1$. For instance, the molar ratio of propylene to the metallocene compound can be at least $1 \times 10^3:1$, $5 \times 10^3:1$, $1 \times 10^4:1$, $5 \times 10^4:1$, or $1 \times 10^5:1$; alternatively or additionally, the maximum molar ratio of propylene to the metallocene compound can be $1 \times 10^9:1$, $5 \times 10^8:1$, $1 \times 10^8:1$, $5 \times 10^7:1$, $1 \times 10^7:1$, $5 \times 10^6:1$, or $1 \times 10^6:1$. Generally, the molar ratio of propylene to the metallocene compound can be in a range from any minimum molar ratio disclosed herein to any maximum molar ratio disclosed herein. Therefore, suitable non-limiting ranges for the molar ratio of propylene to the metallocene compound can include the following ranges: from $1 \times 10^3:1$ to $1 \times 10^9:1$, from $5 \times 10^3:1$ to $1 \times 10^9:1$, from $5 \times 10^3:1$ to $5 \times 10^8:1$, from $1 \times 10^4:1$ to $1 \times 10^8:1$, from $5 \times 10^4:1$ to $1 \times 10^8:1$, from $5 \times 10^4:1$ to $5 \times 10^7:1$, from $1 \times 10^5:1$ to $5 \times 10^7:1$, from $1 \times 10^5:1$ to $1 \times 10^7:1$, from $1 \times 10^5:1$ to $5 \times 10^6:1$, or from $1 \times 10^5:1$ to $1 \times 10^6:1$. Other appropriate ranges for the molar ratio of propylene to the metallocene compound are readily apparent from this disclosure.

Unexpectedly, catalyst systems of the present invention have a high activity. Typically, the catalyst systems have an activity of at least 25,000, at least 30,000, at least 35,000, or at least 40,000 grams of oligomer product per gram of metallocene compound per hour (g/g/hr), and often can range up to 75,000-100,000 g/g/hr. In another embodiment, the activity of the catalyst system can be at least 2,000, at least 3,000, at least 4,000, at least 5,000, or at least 6,000 grams of oligomer product per gram of co-catalyst (when used) per hour, and often can range up to 10,000-15,000 g/g/hr. Generally, the activity of the catalyst system can be measured at 70-80° C., a minimum molar ratio of propylene to the metallocene compound of $1 \times 10^3:1$, and a reactor pressure of 500-550 psig.

Lubricant Compositions

This invention also contemplates and encompasses any compositions (e.g., lubricant compositions or lubricant formulations) or base oils that comprise the propylene oligomers or heavy propylene oligomers (or the hydrogenated propylene oligomers or the hydrogenated heavy propylene oligomers) disclosed herein.

In an embodiment, the propylene oligomers or heavy propylene oligomers (or the hydrogenated propylene oligomers or the hydrogenated heavy propylene oligomers) disclosed herein can be further used in a variety of components or products for a diverse range of applications and industries. For example, the propylene oligomers or heavy propylene oligomers (or the hydrogenated propylene oligomers or the hydrogenated heavy propylene oligomers) can be utilized as a lubricant base oil (or a component of a lubricant base oil) for lubricant compositions and/or functional fluid compositions. Exemplary lubricant compositions in which the propylene oligomers or heavy propylene oligomers (or the hydrogenated propylene oligomers or the hydrogenated heavy propylene oligomers) can be utilized include, but are not limited to, greases, gearbox oils, engine oils, transmission fluids, and/or drilling fluids. Exemplary functional fluid compositions in which the propylene oligomers or heavy propylene oligomers (or the hydrogenated propylene oligomers or the hydrogenated heavy propylene oligomers) can be utilized include, but are not limited to, hydraulic fluids, drilling fluids, coolant fluids, and/or dielectric coolant fluids. In an embodiment, the propylene oligomers or heavy propylene oligomers (or the hydrogenated propylene oligomers or the hydrogenated heavy propylene oligomers) described herein can be utilized as the sole base oil for a lubricant composition and/or functional fluid composition. In other embodiments, the propylene oligomers or heavy propylene oligomers (or the hydrogenated propylene oligomers or the hydrogenated heavy propylene oligomers) described herein can be combined with one or more other base oils to form a base oil for a lubricant composition and/or functional fluid composition. In an embodiment, the propylene oligomers or heavy propylene oligomers (or the hydrogenated propylene oligomers or the hydrogenated heavy propylene oligomers) described herein can be blended with a Group I Base Oil, Group II Base Oil, Group III Base Oil, Group IV Base Oil, a Group V Base Oil, or any combination thereof, to form a lubricant base oil for lubricant compositions and/or functional fluid compositions. As utilized herein, the base oil groups are those as designated by The American Petroleum Institute (API). Additional information on the use of oligomers in lubricant compositions and/or functional fluid compositions can be found in "Synthetic Lubricants and High-Performance Functional Fluids," 2nd Ed., L. Rudnick, ed., Marcel Dekker, Inc., NY (1999). Additional information on additives used in product formulation can be found in "Lubricants and Lubrications," T. Mang and W. Dresel, eds., Wiley-VCH GmbH, Weinheim (2001).

Fully formulated lubricants can further include one or more additives. Additives which can be included in a fully formulated lubricant can include, but are not limited to, viscosity index improvers/viscosity modifiers/viscosity improver, dispersants (metallic and/or non-metallic), detergents (metallic and/or non-metallic), friction modifiers, traction improving additives, demulsifiers, defoamants, antioxidants, anti-wear additives (metallic and non-metallic, phosphorus-containing and non-phosphorus, sulfur-containing and non-sulfur types), extreme-pressure additives (metallic and non-metallic, phosphorus-containing and non-phosphorus, sulfur-containing and non-sulfur types), anti-rust additives, corrosion inhibitors, metal deactivators, anti-seizure agents, pour point depressants, wax modifiers, seal compatibility agents, friction modifiers, lubricity agents, anti-staining agents, chromophores (dyes), and/or haze inhibitors. Additional information on additives used in product formulations can be found in "Fuels and Lubricants Handbook: Technology, Properties, Performance, and Testing" edited by George E. Totten, Steven R. Westbrook, Rajesh J. Shah, ASTM (2003), ISBN 0-8031-2096-6; Chapter 9 Additives and Additive Chemistry, pp. 199-248, "Lubricants and Related Products," Klamann, Verlag Chemie, Deerfield Beach, Fla., ISBN 0-89573-177-0; "Lubricant Additives" by M. W. Ranney, published by Noyes Data Corporation of Parkridge, N.J. (1973); "Lubricants and Lubrications," T. Mang and W. Dresel, eds., Wiley-VCH GmbH, Weinheim (2001); and "Lubricant Additives", C. V. Smallheer and R. K. Smith, published by the Lezius-Hiles Co. of Cleveland, Ohio (1967).

Viscosity index improvers (also known as viscosity modifiers and viscosity improvers) can provide lubricant compositions and/or functional fluid compositions with high and low temperature operability. These additives can impart shear stability at elevated temperatures and acceptable viscosity at low temperatures. Suitable viscosity index improvers can include high molecular weight hydrocarbons, olefin polymers and copolymers, polyesters, and viscosity index improver dispersants that function as both a viscosity index improver and a dispersant. Viscosity index improvers can have molecular weights ranging from about 10,000 Da to about 1,000,000 Da, from about 20,000 Da to about 500,000 Da, or from about 50,000 Da to about 200,000 Da.

Viscosity index improvers can include polymers and copolymers of methacrylate, butadiene, olefins, or alkylated styrenes. Exemplary viscosity index improvers include, but are not limited to, polyisobutylene, copolymers of ethylene and propylene, hydrogenated block copolymers of styrene and isoprene, polyacrylates (e.g., polymers and/or copolymers of various chain length acrylates), and polymethacrylates (e.g., polymers and/or copolymers of various chain length alkyl methacrylates). Generally, the viscosity index improver can be used in an amount of from 0.01 wt. % to 6 wt. %, from 0.01 to 5 wt. %, or from 0.01 to 4 wt. %, based upon the total weight of the composition.

Dispersants are additives utilized to maintain oxidation products (produced during use of the lubricant composition) in suspension in the lubricant compositions and/or functional fluid compositions to prevent the accumulation of debris that could score bearings, block lubricant pathways, prevent deposit formations, inhibit corrosive wear by neutralizing acidic products (e.g., combustion products), and other types of damage. Dispersants can be ash-containing or ashless in character. Dispersants can include, but are not limited to, alkenylsuccinic acid or anhydride derivatives (e.g., succinimides, succinate esters, or succinate ester amides), phenates, Mannich-Base condensates (e.g., the condensation products of alkylphenols, amines and aldehydes), hydrocarbyl substituted amines, sulfonates, sulfurized phenates, salicylates, naphthenates, stearates, carbamates, thiocarbamates, and phosphorus derivatives in metallic and non-metallic versions. Suitable dispersants can contain a polar group attached to a relatively high molecular weight hydrocarbon chain where the polar group contains at least one element of nitrogen, oxygen, or phosphorus. Patents describing dispersants which can be utilized in the lubricant compositions and/or functional fluid compositions include, but are not limited to, U.S. Pat. Nos. 3,036,003; 3,087,936; 3,172,892; 3,200,107; 3,2145,707; 3,219,666; 3,254,025; 3,272,746; 3,275,554; 3,322,670; 3,329,658; 3,316,177; 3,438,757; 3,341,542; 3,413,347; 3,438,757; 3,444,170; 3,449,250; 3,454,555; 3,454,607; 3,519,565; 3,541,012; 3,565,804; 3,630,904; 3,632,511; 3,652,616; 3,666,730; 3,687,849; 3,697,574; 3,702,300; 3,703,536; 3,704,308; 3,725,277; 3,725,480; 3,726,882; 3,751,365; 3,755,433; 3,756,953; 3,787,374; 3,798,165; 3,803,039; 3,822,209; 3,948,800; 4,100,082; 4,234,435; 4,426,305; 4,454,059; 4,767,551; and 5,705,458, among others. Generally, dispersants can be used in an amount from 0.1 wt. % to 20 wt. %, 0.1 wt. % to 15 wt. %, or 0.1 wt. % to 8 wt. %, based upon the total weight of the composition.

Detergents are additives utilized to maintain overall cleanliness by keeping sludge, carbon and deposit precursors suspended in the lubricant compositions and/or functional fluid compositions. Many detergents are chemically similar to dispersants. Detergents which can be utilized in the lubricant compositions and/or functional fluid compositions can include the alkali or alkaline earth metal of sulfates, sulfonates, phenates, carboxylates, phosphates, carboxylic acids, and salicylates. For example, suitable detergents can include, but are not limited to, the sulfonated alkylaromatic hydrocarbons, alkyl phenols, sulfurized alkyl phenols treated with an alkaline earth metal hydroxide or oxide (e.g., CaO, Ca(OH)$_2$, BaO, Ba(OH)$_2$, MgO, or Mg(OH)$_2$). Sulfonated alkylaromatic compounds can be prepared from sulfonic acids obtained by sulfonation of $C_9$ to $C_{80}$ (or $C_6$ to $C_{60}$) alkyl substituted aromatic hydrocarbons (having one or more than one alkyl groups) where the alkyl groups independently can be $C_3$ to $C_{70}$ alkyl groups and the aromatic portion can be benzene, toluene, xylene, naphthalene, or biphenyl. Alkyl phenol and/or sulfurized alkyl phenols can have one or more $C_4$ to $C_{30}$ alkyl groups. The detergents utilized in the lubricant compositions and/or functional fluid compositions can be neutral (i.e., produced using only enough alkali or alkaline earth compound to neutralize the sulfonated alkylaromatic compound, alkyl phenol, or sulfurized alkyl phenol) or can be overbased (i.e., produced using more alkali or alkaline earth compound than necessary to neutralize the sulfonated alkylaromatic compound, alkyl phenol, or sulfurized alkyl phenol). Generally, detergents can be used in an amount from 0.01 wt. % to 6.0 wt. %, 0.05 wt. % to 5.0 wt. %, or 0.1 to 4 wt. %, based upon the total weight of the composition.

Defoamants (or anti-foam agents) are additives utilized to retard the formation of stable foam in the lubricant compositions and/or functional fluid compositions. Defoamants which can be utilized in the lubricant compositions and/or functional fluid compositions can include, but are not limited to, silicone compounds (e.g., polysiloxanes, such as silicon oil or polydimethyl siloxane, among others) and organic polymers. Defoamants can be utilized in conjunction with demulsifiers. Generally, the maximum amount of defoamants can be 1 wt. %, 0.5 wt. %, or 0.1 wt. %, based upon the total weight of the composition.

Antioxidants are additives utilized to retard the oxidative degradation of the base oil(s) in the lubricant compositions and/or functional fluid compositions. Oxidative base oil degradation can produce deposits on metal surfaces, sludge, and/or increase the viscosity of the lubricant composition. Antioxidants which can be utilized in the lubricant compositions and/or functional fluid compositions include, but are not limited to, hindered phenols (ashless); neutral or basic metal salts of hindered phenols; hindered phenolic carboxylic acid (e.g., propionic acid) ester derivatives; bis-hindered phenols; alkylated and non-alkylated aromatic amines; sulfurized alkyl phenols; alkali or alkaline earth metal salts of sulfurized alkyl phenols; copper dihydrocarbyl thio or dithio-phosphates; copper salts of carboxylic acids (natural or synthetic); and copper salts of dithiacarbamates, dithiocarbamates, sulphonates, phenates, acetylacetonates and alkenyl succinic acids or anhydrides (neutral, basic or acidic). Patents describing antioxidants which can be utilized in the lubricant compositions and/or functional fluid compositions include, but are not limited to, U.S. Pat. Nos. 4,798,684 and 5,084,197. Generally, the antioxidants can be used in an amount from 0.01 wt. % to 5 wt. %, from 0.01 to 2.5 wt. %, or from 0.01 wt. % to 1.5 wt. %, based upon the total weight of the composition.

Anti-wear additives and extreme pressure additives are compounds utilized to reduce friction and wear of metal parts of the base oil(s) in the lubricant compositions and/or functional fluid compositions. Anti-wear additives and extreme pressure additives which can be utilized in the lubricant compositions and/or functional fluid compositions include, but are not limited to, metal alkylthiophosphates (e.g., a zinc alkylthiophosphonate having a $C_1$ to $C_{18}$ alkyl group), metal dialkyldithiophosphates (e.g., a zinc alkylthiophosphonate having $C_1$ to $C_{18}$ alkyl groups), sulfurized $C_3$ to $C_{30}$ aliphatic or arylaliphatic hydrocarbon olefins (acyclic or cyclic), polysulfides of thiophosphorus acids, polysulfides of thiophosphorus acid esters, phosphorothionyl disulfides, alkylthiocarbamoyl compounds (e.g., bis(dibutyl)thiocarbamoyl) in combination with a molybdenum compound (e.g., oxymolybdenum diisopropylphosphorodithioate sulfide) and a phosphorus ester (e.g., dibutyl hydrogen phosphite, for example), thiocarbamates, thiocarbamate/molybdenum complexes (e.g., moly-sulfur alkyl dithiocarbamate trimer complexes), and/or glycerol ester (e.g., mono-, di-, and tri-oleates, mono-palmitates and mono-myristates). Patents describing anti-wear additives and/or extreme pressure additives which can be utilized in the lubricant compositions and/or functional fluid compositions include, but are not limited to, U.S. Pat. Nos. 2,443,264; 2,471,115; 2,526,497; 2,591,577; 3,770,854; 4,501,678; 4,941,984; 5,034,141; 5,034,142; 5,084,197; and 5,693,598. Generally, the total amount of anti-wear additives and extreme pressure additives used in the lubricant compositions and/or functional fluid compositions can be from 0.01 wt. % to 6 wt. %, from 0.01 to 5 wt. %, or from 0.01 wt. % to 4 wt. %, based upon the total weight of the composition.

Anti-rust additives are additives that protect lubricated metal surfaces against chemical attack by water or other contaminants. Anti-rust additives can function by 1) wetting the metal surface with a film of oil, 2) absorbing water into a water-in-oil emulsion, and/or 3) adhering to the metal to form a non-reactive surface, among other potential modes of function. Anti-rust additives which can be utilized in the lubricant compositions and/or functional fluid compositions include, but are not limited to, zinc dithiophosphates, metal phenolates, basic metal sulfonates, fatty acids, and amines Generally, the amount of anti-rust additives used in the lubricant compositions and/or functional fluid compositions can be from 0.01 wt. % to 5 wt. %, from 0.01 wt. % to 2.5 wt. %, or from 0.01 wt. % to 1.5 wt. %, based upon the total weight of the composition.

Corrosion inhibitors are additives that reduce the degradation of metallic parts that are in contact with the lubricant compositions and/or functional fluid compositions. Corrosion inhibitors which can be utilized in the lubricant compositions and/or functional fluid compositions include, but are not limited to, thiadiazoles and triazoles. Patents describing corrosion inhibitors which can be utilized in the lubricant compositions and/or functional fluid compositions include, but are not limited to, U.S. Pat. Nos. 2,719,125; 2,719,126; and 3,087,932. Generally, the amount of corrosion inhibitors used in the lubricant compositions and/or functional fluid compositions can be from 0.01 wt. % to 5 wt. %, from 0.01 wt. % to 2.5 wt. %, or from 0.01 wt. % to 1.5 wt. %, based upon the total weight of the composition.

Pour point depressants are additives that reduce the minimum temperature at which the lubricant compositions and/or functional fluid compositions will flow or can be poured. Pour point depressants which can be utilized in the lubricant compositions and/or functional fluid compositions include, but are not limited to, polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Patents describing pour point depressants which can be utilized in the lubricant compositions and/or functional fluid compositions include, but are not limited to, U.S. Pat. Nos. 1,815,022; 2,015,748; 2,191,498; 2,387,501; 2,655,479; 2,666,746; 2,721,877; 2,721,878; and 3,250,715. Generally, the amount of the pour point depressant used in the lubricant compositions and/or functional fluid compositions can be from 0.01 wt. % to 5 wt. %, from 0.01 wt. % to 2.5 wt. %, or from 0.01 wt. % to 1.5 wt. %, based upon the total weight of the composition.

Seal compatibility additives are compounds that swell elastomeric seals and can function by causing a chemical reaction in the fluid or a physical change in the seal elastomer. Seal compatibility additives which can be utilized in the lubricant compositions and/or functional fluid compositions include, but are not limited to, organic phosphates, aromatic esters, aromatic hydrocarbons, esters (e.g., butylbenzyl phthalate), and polybutenyl succinic anhydride. Generally, the amount of the seal compatibility additive used in the lubricant composition and/or functional fluid compositions can be from 0.01 wt. % to 3 wt. %, from 0.01 wt. % to 2.5 wt. %, or from 0.01 wt. % to 2 wt. %, based upon the total weight of the composition.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Kinematic viscosities at 100° C. and 40° C. were determined in accordance with ASTM D7042-04 (Stabinder viscometer method) or ASTM D445 (capillary tube method) at the respective temperatures, and the results are reported in centistokes (cSt). The viscosity index was determined in accordance with ASTM D2270-10e1, using the tables provided therein for viscosity data determined at 100° C. and 40° C. Pour point is a measurement of the temperature at which the sample will begin to flow under carefully controlled conditions. Pour point was determined in accordance with ASTM D97-04 or ASTM D5950 (automatic tilt method), and the results are reported in ° C. Flash point (Cleveland open cup) and Fire Point were determined in accordance with ASTM D92-05.

Molecular weights and molecular weight distributions were obtained using a PL-GPC 220 (Polymer Labs, an Agilent Company) system equipped with a IR4 detector (Polymer Char, Spain) and three Styragel® HMW-6E GPC columns (Waters, Mass.) running at 145° C. The flow rate of the mobile phase 1,2,4-trichlorobenzene (TCB) containing 0.5 g/L 2,6-di-t-butyl-4-methylphenol (BHT) was set at 1 mL/min, and oligomer solution concentrations were in the range of 1.0-1.5 mg/mL, depending on the molecular weight. Sample preparation of the oligomer composition was conducted at 150° C. for nominally 4 hr with occasional and gentle agitation, before the solutions were transferred to sample vials for injection. An injection volume of about 200 µL was used. The integral calibration method was used to deduce molecular weights and molecular weight distributions using a Chevron Phillips Chemicals Company's HDPE polyethylene resin, MARLEX® BHB5003, as the standard (calibration samples of MARLEX® BHB5003 can be obtained from Chevron Phillips Chemicals Company, LP). The integral table of the standard was pre-determined in a separate experiment with SEC-MALS. Mn is the number-average molecular weight, Mw is the weight-average molecular weight, Mz is the z-average molecular weight, and Mp is the peak molecular weight.

Triad determination and the tacticity of the oligomer product, propylene oligomer, and/or the heavy propylene oligomer were determined utilizing $^1$H NMR or $^{13}$C NMR peak intensities and the methods as described in Il Kim, Jia-Min Zhou and Hoeil Chung, "Higher α-Olefin Polymerization by Zr Complex", J. of *Polymer Science: Part A: Polymer Chemistry*, Vol. 38, 1687-1697 (2000).

Chemically-Treated Solid Oxide Preparation

Fluorided silica-coated aluminas (F-SCA) were prepared as follows. Alumina A from W.R. Grace having a surface area of 300 m$^2$/g, a pore volume of 1.2 mL/g, and an average particle size of 100 microns, was first calcined in dry air for 6 hours at 600° C., then cooled to ambient temperature, followed by contacting with tetraethylorthosilicate in isopropanol to equal 25 wt. % $SiO_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. in dry air. Afterward, the fluorided silica-coated alumina (F-SCA) was collected and stored under dry nitrogen, and was used without exposure to the atmosphere.

Fluorided/chlorided silica-coated aluminas (F/Cl-SCA) were prepared as follows, using silica-coated alumina prepared as described above and calcined in dry air at 500° C. for 3 hours. Next, $CCl_4$ was injected and vaporized into a dry air gas stream (typically, over a time period of less than 5 minutes) used to fluidize the silica-coated alumina while calcining at 500° C. (total duration of the calcining operation was 4 hours). Then, tetrafluoroethane was injected and vaporized into the dry air gas stream (typically, over a time period of less than 5 minutes) used to fluidize the chlorided silica-coated alumina while calcining at 500° C. (total duration of the calcining operation was 4.5 hours). Afterward, the fluorided/chlorided silica-coated alumina (4 wt. % Cl+7 wt. % F) was collected and stored under dry nitrogen, and was used without exposure to the atmosphere.

In the examples that follow, MET 1 is bis(n-butylcyclopentadienyl) zirconium dichloride, MET 2 is bis(n-propylcyclopentadienyl) zirconium dichloride, MET 5 is bis(ethylcyclopentadienyl) zirconium dichloride, and MET 4 is $(n-butyl)_2$-Si bridged bis-cyclopentadienyl zirconium dichloride. The chemical structure for the MET 3 is provided below.

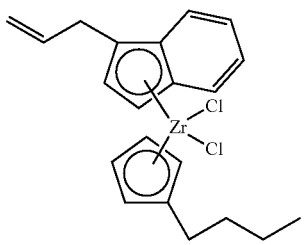

Examples 1-31

Propylene Oligomerization Procedure A

The base of a 1 gallon (3.79 liter) autoclave, under a purge of nitrogen gas, was charged sequentially with the desired chemically-treated solid oxide, triisobutylaluminum (1 molar solution in heptanes), and 2 mL of a 1 mg metallocene per mL of toluene solution containing the designated metallocene. The autoclave was then sealed and charged with 2.5 liters of liquid propylene under a pressure of 150 to 200 psig (1.03 to 1.38 MPa). For experiments which utilized hydrogen, hydrogen was then allowed to flow from a 300 mL pressure vessel charged to 620 psig with hydrogen until the desired pressure drop in the hydrogen charge vessel pressure was achieved. The autoclave was then heated to the desired temperature and the reaction allowed to proceed, with stirring, for one hour. Generally, the reactor pressure was approximately 380 psig (2.62 MPa) for a reaction temperature of 60° C., approximately 440 psig (3.03 MPa) for a reaction temperature of 70° C., approximately 500 psig (3.45 MPa) for a reaction temperature of 75° C., and approximately 520 psig (3.59 MPa) for a reaction temperature of 77° C. The reactor was then cooled to 40° C. The reactor was then vented to a flare line to allow the unreacted propylene to vent from the reactor. The liquid product was collected and filtered to remove the chemically-treated solid oxide. The filtrate was then subjected to rotary evaporation at 100° C. for one hour under a reduced pressure of 5 torr (0.67 kPa) to 10 torr (1.33 kPa). The rotary evaporated liquid was then placed under vacuum, with stirring, at 3 torr (0.40 kPa) and 115° C. or 135° C. for one hour to provide a viscous oil.

Propylene Oligomerization Procedure B

The base of a 1 gallon (3.79 liter) autoclave, under a purge of nitrogen gas, was charged sequentially with the desired chemically-treated solid oxide, triisobutylaluminum (1 molar solution in heptanes), and 2 mL of a 1 mg metallocene per mL of toluene solution containing the designated metallocene. The autoclave was then sealed and charged with 2.5 liters of liquid propylene under a pressure of 150 to 200 psig (1.03 to 1.38 MPa). The autoclave was then heated to the desired temperature and the reaction allowed to proceed, with stirring, for one hour. Hydrogen was charged to the reactor when the reactor reached a temperature of 10° C. below the desired temperature using a Brookes Model SLA5850 mass flow meter at the desired rate. Generally, the reactor pressure was approximately 440 psig (3.03 MPa) for a reaction temperature of 70° C., approximately 500 psig (3.45 MPa) for a reaction temperature of 75° C., and approximately 520 psig (3.59 MPa) for a reaction temperature of 77° C. The reactor was then cooled to 40° C. The reactor was then vented to a flare line to allow the unreacted propylene to vent from the reactor. The liquid product was collected and filtered to remove the chemically-treated solid oxide. The filtrate was then subjected to rotary evaporation at 100° C. for one hour under a reduced pressure of 5 torr (0.67 kPa) to 10 torr (1.33 kPa). The rotary evaporated liquid was the placed under vacuum, with stirring, at 3 torr (0.40 kPa) and 115° C. or 135° C. for one hour to provide a viscous oil.

Propylene Oligomerization Procedure C

The base of a 1 gallon (3.79 liter) autoclave, under a purge of nitrogen gas, was charged sequentially with the desired chemically-treated solid oxide, triisobutylaluminum (1 molar solution in heptanes), and 2 mL of a 1 mg metallocene per mL of toluene solution containing the designated metallocene. The autoclave was then sealed and charged with one liter of heptane and then charged with 2.0 liters of liquid propylene under a pressure of 150 to 200 psig (1.03 to 1.38 MPa). For experiments which utilized hydrogen, hydrogen was then allowed to flow from a 300 mL pressure vessel charged to 620 psig with hydrogen until the desired pressure drop in the hydrogen charge vessel pressure was achieved. The autoclave was then heated to the desired temperature and the reaction allowed to proceed, with stirring, for one hour. Generally, the reactor pressure was approximately 440 psig (3.03 MPa) for a reaction temperature of 70° C., approximately 500 psig (3.45 MPa) for a reaction temperature of 75° C., and approximately 520 psig (3.59 MPa) for a reaction temperature of 77° C. The reactor was then cooled to 40° C. The reactor was then vented to a flare line to allow the unreacted propylene to vent from the reactor. The liquid product was collected and filtered to remove the chemically-treated solid oxide. The filtrate was then subjected to rotary evaporation at 100° C. for one hour under a reduced pressure of 5 torr (0.67 kPa) to 10 (1.33 kPa) torr. The rotary evaporated liquid was the placed under vacuum, with stirring, at 3 torr (0.40 kPa) and 115° C. or 135° C. for one hour to provide a viscous oil.

Propylene Oligomerization Procedure D

The base of a 1 gallon (3.79 liter) autoclave, under a purge of nitrogen gas, was charged sequentially with the desired chemically-treated solid oxide, triisobutylaluminum (1 molar solution in heptanes), and 2 mL of a 1 mg metallocene per mL of toluene solution containing the designated metallocene. The autoclave was then sealed and charged with 2 liters of isobutane. The desired amount of propylene was then added via syringe pump over the course of the run to maintain a pressure of 220 psig (1.52 MPa). For experiments which utilized hydrogen, hydrogen was fed as a set ratio to the amount of propylene as it was delivered from the syringe pump. The autoclave was then heated to the desired temperature and the reaction allowed to proceed, with stirring, for one hour. The reactor was then cooled to 40° C. The reactor was then vented to a flare line to allow the unreacted propylene to vent from the reactor. The liquid product was collected and filtered to remove the chemically-treated solid oxide. The filtrate was then subjected to rotary evaporation at 100° C. for one hour under a reduced pressure of 5 torr (0.67 kPa) to 10 torr (1.33 kPa). The rotary evaporated liquid was the placed under vacuum, with stirring, at 3 torr (0.40 kPa) and 115° C. or 135° C. for one hour to provide a viscous oil.

Summary of Experimental Results for Examples 1-33

In some of Examples 1-32, a molecular weight distribution of the liquid product prior to the filtration step to remove the chemically-treated solid oxide was determined using the gel permeation chromatography method described herein. In some of Examples 1-32, a molecular weight distribution of the viscous oil obtained after subjecting the rotary evaporated liquid placed under vacuum, with stirring, at 3 torr (0.40 kPa) and 115° C. or 135° C. for one hour was determined using the gel permeation chromatography method described herein. In some of Examples 1-32, the 40° C. and 100° C. kinematic viscosities, viscosity index, pour point, flash point and fire points for the viscous oil obtained after subjecting the rotary evaporated liquid placed under vacuum, with stirring, at 3 torr (0.40 kPa) and 115° C. or 135° C. for one hour were measured using the methods indicated herein.

Table I summarizes the metallocene, propylene oligomerization procedure, oligomerization conditions, product weights, and activities for Examples 1-32. In Table I, Ex is the Example number, Pro is the propylene oligomerization procedure (A, B, C, or D), MET is the metallocene compound(s) used, MET (mg) is the weight of the metallocene compound(s) used, CTSO is the chemically-treated solid oxide used, CTSO (mg) is the weight of the chemically-treated solid oxide used, TIBA (mL) is the amount of a 1M triisobutylaluminum solution of co-catalyst used, $\Delta H_2$ is the amount of hydrogen used (based on pressure drop), Temp is the oligomerization reaction temperature used, Time is the reaction time, Prod Wt. (g) is the weight of the oligomer product produced prior to rotary evaporation, and the catalyst activities shown are based on the Zr metal (g oligomer product per gram of Zr per hour-g product/g Zr/hr), based on the Al in the TIBA co-catalyst (g oligomer product per gram of Al per hour-g product/g Al/hr), and based on the CTSO (g oligomer product per gram of CTSO per hour-g product/g CTSO/hr). As shown in Table I, and unexpectedly, catalyst activities were increased for examples that were performed in the presence of hydrogen, in comparison to those examples in which no hydrogen was added during polymerization.

Table II provides the molecular weight distribution data for the liquid product prior to the filtration step to remove the chemically-treated solid oxide (if determined), the molecular weight distribution data for the viscous oil obtained after subjecting the rotary evaporated liquid placed under vacuum, with stirring, at 3 torr (0.40 kPa) and 115° C. or 135° C. for one hour (if determined), and the physical properties (40° C. and 100° C. kinematic viscosities, viscosity index, pour point, flash point and fire points) for the viscous oil obtained after subjecting the rotary evaporated liquid placed under vacuum, with stirring, at 3 torr (0.40 kPa) and 115° C. or 135° C. for one hour (if determined) for Examples 1-32. In Table II, Ex is the example number, the molecular weight properties are shown in kg/mol, VI is the viscosity index, Vis 40 is the 40° C. kinematic viscosity in cSt, Vis 100 is the 100° C. kinematic viscosity in cSt, Flash/Fire are the respective flash and fire points (° C.), and Pour Point is shown in ° C. Example 33 represents a commercial sample of Bright Stock (Kendex® 0847), which is a high viscosity oil obtained from heavy residues of petroleum distillation, and is frequently used in lubricant formulations.

As shown in Table II, the crude oligomer products produced in Examples 1-32 had Mn's ranging from 310 to 1610 g/mol, and the ratios of Mz/Mw ranged from 1.89 to 6.75. The propylene oligomers, after volatile removal at 100° C. or 135° C., had Mn's ranging from 830 to 2120 g/mol, and the ratios of Mz/Mw ranged from 1.78 to 5.91. The viscosity index ranged from 44 to 121, the viscosity at 40° C. ranged from 230 to 2882 cSt, the viscosity at 100° C. ranged from 20.9 to 107.4 cSt, the pour point ranged from −30° C. to −10° C., and the flash point ranged from 149 to 229° C. for the propylene oligomers tested. Table II demonstrates, with the exception of the flash point, that propylene oligomers were produced having properties that are comparable to, or better than, that of the Bright Stock sample of Example 33.

The amount of isotactic triads (mm triads), atactic triads (mr triads), and syndiotactic triads (rr triads) were determined for the final propylene oligomers of certain examples by $^1$H NMR or $^{13}$C NMR peak intensities as described by per Il Kim, Jia-Min Zhou and Hoeil Chung, "Higher α-Olefin Polymerization by Zr Complex", J. of *Polymer Science: Part A: Polymer Chemistry*, Vol. 38, 1687-1697 (2000). Generally, the percentage of triads satisfy the formula mm triads+mr triads+rr triad=100. Table III provides the results of the $^1$H NMR or $^{13}$C NMR peak intensity analysis of the certain examples, and the propylene oligomers had mr triad contents (atactic contents) in a fairly narrow range of 44.6% to 48.2%.

TABLE I

| Ex | Pro | MET | MET (mg) | CTSO | CTSO (mg) | TIBA (mL) | Δ H₂ (psig) | Temp (° C.) | Time (min) | Prod Wt. (g) | Activities (g product/g Zr, Al, or CTSO/hour) Based on Zr | Based on Al | Based on CTSO |
|---|---|---|---|---|---|---|---|---|---|---|---|---|---|
| 1 | A | MET 3 | 2 | F/Cl-SCA | 300 | 0.5 | 0 | 70 | 60 | 37 | 89,000 | 2,600 | 123 |
| 2 | A | MET 3 | 2 | F/Cl-SCA | 300 | 0.5 | 50 | 70 | 60 | 154 | 370,000 | 11,000 | 513 |
| 3 | A | MET 3 | 2 | F-SCA | 300 | 0.5 | 50 | 70 | 60 | 190 | 457,000 | 13,600 | 633 |
| 4 | A | MET 3 | 2 | F-SCA | 300 | 0.5 | 50 | 75 | 60 | 144 | 346,000 | 10,300 | 480 |
| 5 | A | MET 3 | 2 | F-SCA | 600 | 0.5 | 3 * 20± | 70 | 60 | 162 | 389,000 | 11,600 | 270 |
| 6 | A | MET 3 | 2 | F-SCA | 300 | 0.5 | 5 * 10† | 70 | 60 | 134 | 322,000 | 9,580 | 447 |
| 7[a] | D | MET 3 | 2 | F-SCA | 300 | 0.5 | 0 | 70 | 60 | 3 | 7,210 | 214 | 10 |
| 8[b] | D | MET 3 | 2 | F-SCA | 300 | 0.5 | 10 | 70 | 60 | 23.3 | 56,000 | 1,670 | 78 |
| 9[c] | D | MET 3 | 2 | F-SCA | 300 | 0.5 | 25 | 70 | 60 | 10.3 | 24,800 | 736 | 34 |
| 10 | B | MET 3 | 2 | F-SCA | 300 | 0.5 | 1[d] | 70 | 60 | 138 | 332,000 | 9,860 | 460 |
| 11 | B | MET 3 | 2 | F-SCA | 300 | 0.5 | 1.5[d] | 70 | 60 | 100 | 240,000 | 7,150 | 333 |
| 12 | B | MET 3 | 2 | F-SCA | 300 | 0.5 | 0.5[d] | 70 | 60 | 98 | 236,000 | 7,000 | 327 |
| 13 | A | MET 2 | 2 | F-SCA | 300 | 0.5 | 0 | 70 | 60 | 26 | 53,600 | 1,860 | 87 |
| 14 | A | MET 2 | 2 | F-SCA | 300 | 0.5 | 50 | 75 | 60 | 190 | 392,000 | 13,600 | 633 |
| 15 | A | MET 2 | 2 | F-SCA | 300 | 0.5 | 50 | 70 | 60 | 153 | 316,000 | 10,900 | 510 |
| 16 | A | MET 2 | 2 | F-SCA | 300 | 0.5 | 4 * 20‡ | 70 | 60 | 116 | 239,000 | 8,290 | 387 |
| 17 | A | MET 2 | 2 | F-SCA | 600 | 0.5 | 50 | 70 | 60 | 242 | 499,000 | 17,300 | 403 |
| 18 | A | MET 1 | 2 | F-SCA | 300 | 0.5 | 0 | 70 | 60 | 27 | 59,900 | 1,930 | 90 |
| 19 | A | MET 1 | 2 | F-SCA | 300 | 0.5 | 50 | 70 | 60 | 161 | 357,000 | 11,510 | 537 |
| 20 | A | MET 1 | 2 | F-SCA | 300 | 0.5 | 50 | 75 | 60 | 169 | 375,000 | 12,100 | 563 |
| 21 | A | MET 1 | 2 | F-SCA | 300 | 0.5 | 80 | 75 | 60 | 135 | 299,000 | 9,650 | 450 |
| 22 | A | MET 1 | 2 | F-SCA | 600 | 0.5 | 50 | 75 | 60 | 246 | 545,000 | 17,600 | 410 |
| 23 | B | MET 4 | 2 | F-SCA | 300 | 0.5 | 0 | 70 | 60 | 64 | 152,000 | 4,580 | 213 |
| 24 | B | MET 4 | 2 | F-SCA | 300 | 0.5 | 0.5[d] | 70 | 60 | 59.4 | 141,000 | 4,250 | 198 |
| 25 | B | MET 4 | 2 | F-SCA | 300 | 0.5 | 1[d] | 70 | 60 | 69.6 | 165,000 | 4,980 | 232 |
| 26 | B | MET 4 | 2 | F-SCA | 300 | 0.5 | 3[d] | 70 | 60 | 131 | 311,000 | 9,360 | 437 |
| 27 | A | MET 4 | 2 | F-SCA | 300 | 0.5 | 50 | 75 | 60 | 121 | 287,000 | 8,650 | 403 |
| 28 | A | MET 4 | 2 | F/Cl-SCA | 300 | 0.5 | 0 | 75 | 60 | 206 | 488,000 | 14,700 | 687 |
| 29 | A | MET 5 | 2 | F-SCA | 300 | 0.5 | 50 | 60 | 60 | 196 | 374,000 | 1,980 | 653 |
| 30 | A | MET 1/ MET 2 | 1/1 | F-SCA | 300 | 0.5 | 50 | 75 | 60 | 123 | 263,000 | 1,240 | 410 |
| 31 | C | MET 3 | 2 | F-SCA | 300 | 0.5 | 50 | 70 | 60 | 50* | 119,000 | 3,750 | 167 |
| 32 | A | MET 1 | 2 | F-SCA | 300 | 0.5 | 50 | 70 | 60 | 78* | 185,000 | 5,580 | 260 |

[a]Charged 413 mL of propylene.
[b]Charged 557 mL of propylene and 10 ppm by mass hydrogen based upon mass of propylene.
[c]Charged 441 mL of propylene and 25 ppm by mass hydrogen based upon mass of propylene.
±One initial addition of a 20 psig pressure drop followed by additional hydrogen additions of a 20 psig pressure drop at 20 and 40 minutes.
†One initial addition of a 10 psig pressure drop followed by additional hydrogen additions of a 10 psig pressure drop at 12, 24, 36, and 48 minutes.
‡One initial addition of a 20 psig pressure drop followed by additional hydrogen additions of a 20 psig pressure drop at 15, 30, and 45 minutes.
*Product mass of final viscous oil.
[d]Rate, in mg H₂ per minute, at which hydrogen was metered into the reaction vessel.

TABLE II

| | Molecular Weight Distribution Data (molecular weights in kg/mol) | | | | | | | Properties After Volatile Component Removal | | | | |
|---|---|---|---|---|---|---|---|---|---|---|---|---|
| Ex | Mn | Mw | Mz | Mv | Mp | Mw/Mn | Mz/Mw | VI | Vis 40 (cSt) | Vis 100 (cSt) | Flash/ Fire | Pour Point |
| 1 Crude Product After Volatile Removal | 0.96 | 3.17 | 8.29 | 2.79 | 2.23 | 3.3 | 2.62 | | | | | |
| 2 Crude Product After Volatile Removal | 1.02 | 2.68 | 5.48 | 2.43 | 2.07 | 2.63 | 2.05 | | | | | |
| 3 Crude Product After Volatile Removal† | 0.7 0.92 | 2.16 2.42 | 5.03 6.57 | 1.93 2.15 | 1.59 1.69 | 3.09 2.63 | 3.32 2.71 | 94.5 | 509 | 32.3 | 177/227 | −23 |
| 4 Crude Product After Volatile Removal | 0.8 | 2.52 | 9.35 | 2.17 | 1.57 | 3.15 | 3.71 | | | | | |
| 5 Crude Product After Volatile Removal† | 0.91 | 2.26 | 4.84 | 2.05 | 1.66 | 2.48 | 2.14 | 93.5 | 465 | 30.2 | 172/224 | −28 |
| 6 Crude Product After Volatile Removal‡ | 1.33 1.51 | 2.69 2.85 | 5.31 5.58 | 2.47 2.63 | 1.99 1.99 | 2.02 1.89 | 1.97 1.96 | 90.0 | 938 | 47.6 | 178/226 | −15 |

TABLE II-continued

|  |  | Molecular Weight Distribution Data (molecular weights in kg/mol) |  |  |  |  |  | Properties After Volatile Component Removal |  |  |  |  |
|---|---|---|---|---|---|---|---|---|---|---|---|---|
| Ex |  | Mn | Mw | Mz | Mv | Mp | Mw/Mn | Mz/Mw | VI | Vis 40 (cSt) | Vis 100 (cSt) | Flash/Fire | Pour Point |
| 7 | Crude Product After Volatile Removal | 0.45 | 1.49 | 8.27 | 1.22 | 0.36 | 3.31 | 5.55 |  |  |  |  |  |
| 8 | Crude Product After Volatile Removal | 0.32 | 1.15 | 4.21 | 0.97 | 0.38 | 3.59 | 3.66 |  |  |  |  |  |
| 9 | Crude Product After Volatile Removal | 0.31 | 1.15 | 4.81 | 0.96 | 0.31 | 3.71 | 4.18 |  |  |  |  |  |
| 10 | Crude Product After Volatile Removal | 0.69 | 2.29 | 5.31 | 2.04 | 1.78 | 3.34 | 2.32 |  |  |  |  |  |
| 11 | Crude Product After Volatile Removal | 0.73 | 2.22 | 4.99 | 1.99 | 1.70 | 3.06 | 2.25 |  |  |  |  |  |
| 12 | Crude Product After Volatile Removal | 0.69 | 2.38 | 6.26 | 2.09 | 1.86 | 3.44 | 2.63 |  |  |  |  |  |
| 13 | Crude Product After Volatile Removal | 0.51 | 2.74 | 13.78 | 2.24 | 1.48 | 5.37 | 5.03 |  |  |  |  |  |
| 14 | Crude Product After Volatile Removal‡ | 0.57 1.3 | 2.28 3.26 | 7.07 14.31 | 1.95 2.81 | 1.41 1.72 | 4.00 2.51 | 3.10 4.39 | 121.0 | 498 | 34.9 | 149/209 | −25 |
| 15 | Crude Product After Volatile Removal | 0.65 | 3.07 | 13.89 | 2.54 | 1.62 | 4.72 | 4.52 | 110.0 | 540 | 38.1 | 175/221 | −23 |
| 16 | Crude Product After Volatile Removal† | 0.92 | 3.29 | 19.46 | 2.72 | 1.74 | 3.58 | 5.91 | 97.7 | 615 | 37.6 | 190/224 | −20 |
| 17 | Crude Product After Volatile Removal† | 0.83 | 2.66 | 7.54 | 2.32 | 1.66 | 3.20 | 2.83 | 107.4 | 407 | 30.8 | 164/206 | −27 |
| 18 | Crude Product After Volatile Removal | 0.46 | 2.3 | 9.87 | 1.90 | 1.45 | 5.00 | 4.29 |  |  |  |  |  |
| 19 | Crude Product After Volatile Removal | 0.57 | 2.42 | 6.62 | 2.09 | 1.55 | 4.25 | 2.74 |  |  |  |  |  |
| 20 | Crude Product After Volatile Removal‡ | 0.58 1.28 | 2.26 3.01 | 6.7 10.16 | 1.95 2.64 | 1.37 1.62 | 3.9 2.35 | 2.96 3.38 | 110 | 540 | 38.1 | 175/221 | −23 |
| 21 | Crude Product After Volatile Removal | | | | | | | | 107.5 | 230 | 20.9 | 164/206 | −30 |
| 22 | Crude Product After Volatile Removal | | | | | | | | 101.6 | 313 | 24.8 | 172/218 | −26 |
| 23 | Crude Product After Volatile Removal | 0.8 | 3.93 | 26.51 | 3.18 | 1.97 | 4.91 | 6.75 |  |  |  |  |  |
| 24 | Crude Product After Volatile Removal | 0.71 | 2.43 | 5.16 | 2.19 | 1.85 | 3.42 | 2.12 |  |  |  |  |  |
| 25 | Crude Product After Volatile Removal | 0.75 | 2.6 | 5.73 | 2.34 | 2.03 | 3.47 | 2.20 |  |  |  |  |  |
| 26 | Crude Product After Volatile Removal | 0.79 | 2.6 | 5.32 | 2.35 | 2.06 | 3.29 | 2.05 |  |  |  |  |  |
| 27 | Crude Product After Volatile Removal‡ | 1.33 1.54 | 2.83 2.90 | 5.35 5.15 | 2.61 2.70 | 2.32 2.29 | 2.13 1.88 | 1.89 1.78 | 103.0 | 1176 | 60.0 | 165/211 | −15 |
| 28 | Crude Product After Volatile Removal‡ | 1.61 2.12 | 3.69 4.26 | 7.12 7.96 | 3.39 3.93 | 3.02 3.41 | 2.29 2.01 | 1.93 1.87 | 44.0 | 2882 | 63.7 | 229/237 | −11 |
| 29 | Crude Product After Volatile Removal‡ | 0.82 1.55 | 3.12 3.67 | 9.34 9.47 | 2.7 3.27 | 1.89 2.11 | 3.8 2.37 | 2.99 2.58 | n/a | n/a | 107.4 | 212/230 | −10 |
| 30 | Crude Product After Volatile Removal‡ | 1.00 1.32 | 2.30 2.57 | 4.97 5.43 | 2.08 2.36 | 1.75 1.68 | 2.30 1.95 | 2.16 2.11 | 115.0 | 470 | 35.7 | 197/243 | −22 |

TABLE II-continued

| | Molecular Weight Distribution Data (molecular weights in kg/mol) | | | | | | | Properties After Volatile Component Removal | | | | |
|---|---|---|---|---|---|---|---|---|---|---|---|---|
| Ex | Mn | Mw | Mz | Mv | Mp | Mw/Mn | Mz/Mw | VI | Vis 40 (cSt) | Vis 100 (cSt) | Flash/ Fire | Pour Point |
| 31 Crude Product | 0.59 | 1.75 | 4.46 | 1.55 | 1.27 | 2.97 | 2.55 | | | | | |
| After Volatile Removal | 0.8 | 1.91 | 4.84 | 1.71 | 1.11 | 2.39 | 2.53 | | | | | |
| 32 Crude Product | 0.58 | 2.26 | 6.70 | 1.95 | 1.37 | 3.90 | 2.96 | | | | | |
| After Volatile Removal | 1.28 | 3.01 | 10.16 | 2.64 | 1.62 | 2.35 | 3.38 | | | | | |
| 33 Bright Stock | | | | | | | | 97.0 | 485 | 32.0 | 293 | −12 |

†The volatiles were removed at 100° C.
‡The volatiles were removed at 135° C.

TABLE III

| Example | Isotactic | Atactic | Syndiotactic |
|---|---|---|---|
| 3 | 29.9 | 44.6 | 25.5 |
| 5 | 28.3 | 46.3 | 25.4 |
| 16 | 24.5 | 47.7 | 28.1 |
| 17 | 23.8 | 48.2 | 28.0 |

Examples 34-36

A slurry of fluorided silica-coated alumina, triisobutylaluminum (1 molar solution in heptanes), 2 mL of a 1 mg metallocene MET 3 per mL of toluene, and 2 mL hexanes was prepared and syringed into a 1 gallon (3.79 liter) autoclave, under a purge of nitrogen gas. The autoclave was then charged with 2.5 liters of liquid propylene under a pressure of 150 to 200 psig (1.03 to 1.38 MPa) and 86 mg of hydrogen. The autoclave was then heated to 77° C. and the reaction allowed to proceed, with stirring at 1000 rpm, for one hour. Generally, the reactor pressure was approximately 520 psig (3.59 MPa) at the 77° C. reaction temperature. The reactor was then cooled to 40° C. The reactor was then vented to a flare line to allow the unreacted propylene to vent from the reactor. The raw liquid product was then collected. The molecular weight distribution of the raw liquid product was determined using the gel permeation chromatography method described herein.

The raw liquid product was then subjected to vacuum at <2 torr (<0.27 kPa) and 135° C. to remove the light hydrocarbons. The resulting oil was then diluted in heptane and filtered to remove the support and other solid impurities. The filtrate was then subjected to vacuum at <2 torr (<0.27 kPa) and 135° C., with stirring, for at least 15 minutes to provide a viscous oil. The molecular weight distribution of the final viscous oil was determined using the gel permeation chromatography method described herein. The final viscous oils of Examples 34-36 were combined and the 40° C. and 100° C. kinematic viscosities, viscosity index, pour point, and flash point of the combined viscous oil were measured using the methods indicated herein.

Examples 37-40

A solution of methylaluminoxane (10 wt. % solution in toluene), 2 mL of a 1 mg metallocene MET 3 per mL of toluene, and 2 mL hexanes was prepared and syringed into a 1 gallon (3.79 liter) autoclave, under a purge of nitrogen gas. The autoclave was then charged with 2.5 liters of liquid propylene under a pressure of 150 to 200 psig (1.03 to 1.38 MPa) and 86 mg of hydrogen. The autoclave was then heated to 77° C. and the reaction allowed to proceed, with stirring at 1000 rpm, for one hour. Generally, the reactor pressure was approximately 520 psig (3.59 MPa) at the 77° C. reaction temperature. The reactor was then cooled to 40° C. The reactor was then vented to a flare line to allow the unreacted propylene to vent from the reactor. The raw liquid product was then collected. The molecular weight distribution of some of the raw liquid products was determined using the gel permeation chromatography method described herein.

The raw liquid product was then subject to vacuum at <2 torr (<0.27 kPa) and 135° C. to remove the light hydrocarbons. The resulting oil was then diluted in heptane and filtered to remove the support and other solid impurities. The filtrate was then subjected to vacuum at <2 torr (<0.27 kPa) and 135° C., with stirring, for at least 15 minutes to provide a viscous oil. The molecular weight distribution of some of the final viscous oil was determined using the gel permeation chromatography method described herein. The final viscous oils of Examples 37-40 were combined and the 40° C. and 100° C. kinematic viscosities, viscosity index, pour point, and flash point of the combined viscous oil were measured using the methods indicated herein.

Examples 41-44

Preparation of Silica-Supported MAO

Silica, 150 mL of ES70X, was calcined by heating at 4° C./minute to 180° C. under a nitrogen stream (1.2 SCFH) and held at 180° C. for 3 hours. The silica was then allowed to cool to ambient temperature under a nitrogen stream overnight. The silica was then calcined a second time by heating at 4° C./minute to 180° C. under a nitrogen stream (1.2 SCFH) and held at 180° C. for 3 hours. The silica was allowed to cool to ambient temperature, and packaged.

In a nitrogen glove box, the calcined ES70X silica (5.0 g) was slurried in 25 g of toluene. Methylaluminoxane (15 mL, 10 wt. % in toluene) was slowly added while maintaining the slurry at a temperature of 25° C.-28° C. The slurry was stirred for two hours and then filtered. The filtered solid was then rinsed two times with 25 mL of toluene and then rinsed two times with 5 mL of hexanes. The rinsed solids were then dried under vacuum for 5 hours at approximately 5 torr (0.67 kPa) to provide 5.6 g of silica supported methylaluminoxane.

In a nitrogen glove box, a 20 mL vial was charged with 65 mg of metallocene MET 3, 5 mL of toluene, and methylaluminoxane (15 mL, 10 wt. % in toluene). The contents of the vial were then slurried for one hour. A 2 g sample of the silica supported methylaluminoxane (prepared as described herein) was placed on a filter frit and wetted with 10 mL of toluene. The excess toluene was allowed to pass through frit and the MAO treated metallocene solution was slowly poured over the toluene wetted silica supported methylaluminoxane. A slight vacuum was pulled on the frit until the top of the metallocene solution was level with the top of the silica supported methylaluminoxane. The mixture was then stirred with a spatula to thoroughly mix the metallocene solution and the silica supported methylaluminoxane. The mixture was then allowed to stand for 1 hour. The slurry was then rinsed three times with 5 mL with hexanes and dried with a nitrogen purge for 1 hour at ambient temperature to provide 2.58 g of silica supported methylaluminoxane/metallocene MET 3.

Propylene Oligomerization Procedure

The base of a 1 gallon (3.79 liter) autoclave, under a purge of nitrogen gas, was charged sequentially with triisobutylaluminum (1 molar solution in heptanes) and the silica supported methylaluminoxane/metallocene MET 3 (containing 2 mg of metallocene MET 3). The autoclave was then charged with 2.5 liters of liquid propylene under a pressure of 150 to 200 psig (1.03 to 1.38 MPa) and 86 mg of hydrogen. The autoclave was then heated to 77° C. and the reaction allowed to proceed, with stirring at 1000 rpm, for one hour. Generally, the reactor pressure was approximately 520 psig (3.59 MPa) at the 77° C. reaction temperature. The reactor was then cooled to 40° C. The reactor was then vented to a flare line to allow the unreacted propylene to vent from the reactor. The raw liquid product was then collected. The molecular weight distribution of some of the raw liquid products was determined using the gel permeation chromatography method described herein.

The raw liquid product was then subject to vacuum at <2 torr (<0.27 kPa) and 135° C. to remove the light hydrocarbons. The resulting oil was then diluted in heptane and filtered to remove the support and other solid impurities. The filtrate was then subjected to vacuum at <2 torr (<0.27 kPa) and 135° C., with stirring, for at least 15 minutes to provide a viscous oil. The molecular weight distribution of some of the final viscous oil was determined using the gel permeation chromatography method described herein. The final viscous oils of Examples 41-44 were combined and the 40° C. and 100° C. kinematic viscosities, viscosity index, pour point, and flash point of the combined viscous oil were measured using the methods indicated herein.

Summary of Experimental Results for Examples 34-44

Table IV summarizes certain catalyst system components, oligomerization conditions, product weights, and activities for examples 34-44. In Table IV, Ex is the Example number, MET 3 (mg) is the weight of the MET 3 metallocene compound used, Support is the support used, Support (mg) is the weight of the support used, Aluminum compound and Aluminum compound (mL) specify the aluminum compounds used and the respective amounts, Temp is the oligomerization reaction temperature used, Time is the reaction time, Prod Wt. (g) is the mass of the crude oligomer product prior to rotary evaporation, and the catalyst activities shown are based on the Zr metal (g oligomer product per gram of Zr per hour-g product/g Zr/hr), based on the Al in the TIBA or MAO (g oligomer product per gram of Al per hour-g product/g Al/hr), and based on the support (g oligomer product per gram of support per hour-g product/g support/hr). As shown in Table IV, and unexpectedly, the catalyst system used in Examples 34-36 had the highest catalyst activity.

Table V provides the molecular weight distribution data for the liquid product prior to the filtration step to remove the catalyst system (if determined), the molecular weight distribution data for the viscous oil obtained after subjecting the rotary evaporated liquid placed under vacuum, with stirring, at 3 torr (0.40 kPa) and 135° C. for one hour (if determined), and the physical properties (40° C. and 100° C. kinematic viscosities, viscosity index, pour point, and flash point) for the combined viscous oils. In Table V, Ex is the example number, the molecular weight properties are shown in kg/mol, VI is the viscosity index, Vis 40 is the 40° C. kinematic viscosity in cSt, Vis 100 is the 100° C. kinematic viscosity in cSt, Flash Point is shown in ° C., and Pour Point is shown in ° C.

As shown in Table V, Examples 34-36 had the lowest Mn's (ranging from 700 to 1030 g/mol) and generally the highest ratios of Mz/Mw. The FIGURE illustrates the molecular weight distributions of the "distilled" propylene oligomers of Examples 34-44, after volatiles removal. Unexpectedly, the propylene oligomers of Examples 34-36 (represented by Example 34) had noticeably different molecular weight distribution curves than Examples 37-40 (represented by Example 37) and Examples 41-44 (represented by Example 42). In particular, the propylene oligomers of Examples 34-36 included a low molecular weight shoulder, and the molecular weight curve was shifted to the left, indicating these propylene oligomers had lower molecular weights.

Table V also demonstrates, quite surprisingly, the combined propylene oligomers of Examples 34-36 (resulting from a catalyst system containing a chemically-treated solid oxide) had a significantly higher viscosity index (equal to 92) and a significantly lower pour point (equal to −26° C.), as compared to propylene oligomers produced using catalyst systems with a MAO activator (Examples 37-40 and Examples 41-44).

Table VI summarizes the tacticity analysis of the combined propylene oligomers of Examples 34-36, Examples 37-40, and Examples 41-44 at the triad level. Interestingly, the propylene oligomers had mr triad (atactic) contents in a fairly narrow range of 46.7% to 48%.

TABLE IV

| Ex | Met 3 (mg) | Support | Support (mg) | Aluminum Compound | Aluminum Compound (mL) | Temp (° C.) | Time (min) | Prod Wt. (g) | Activities (g product/g Zr, Al, or support/hour) | | |
|----|------|-------|------|------|-----|----|----|-----|---------|-------|-----|
| | | | | | | | | | Based on Zr | Based on Al | Based on support |
| 34 | 2 | F-SCA | 300 | TIBA | 0.5 | 77 | 60 | 126 | 303,000 | 1,270 | 420 |
| 35 | 2 | F-SCA | 300 | TIBA | 0.5 | 77 | 60 | 112 | 269,000 | 1,130 | 373 |
| 36 | 2 | F-SCA | 300 | TIBA | 0.5 | 77 | 60 | 95 | 228,000 | 960 | 317 |
| 37 | 2 | — | — | MAO | 1.8 | 77 | 60 | 105 | 252,000 | 667 | NA |
| 38 | 2 | — | — | MAO | 1.8 | 77 | 60 | 103 | 248,000 | 654 | NA |

TABLE IV-continued

| | | | | Aluminum | | | Prod | Activities (g product/g Zr, Al, or support/hour) | | |
|---|---|---|---|---|---|---|---|---|---|---|
| Ex | Met 3 (mg) | Support | Support (mg) | Aluminum Compound | Compound (mL) | Temp (° C.) | Time (min) | Wt. (g) | Based on Zr | Based on Al | Based on support |
| 39 | 2 | — | — | MAO | 1.8 | 77 | 60 | 106 | 255,000 | 673 | NA |
| 40 | 2 | — | — | MAO | 1.8 | 77 | 60 | 88 | 212,000 | 559 | NA |
| 41 | 2 | MAO/Silica | 80 | TIBA | 0.5 | 77 | 60 | 25 | 60,900 | — | 312 |
| 42 | 2 | MAO/Silica | 240 | TIBA | 0.5 | 77 | 60 | 43 | 101,000 | — | 179 |
| 43 | 2 | MAO/Silica | 240 | TIBA | 0.5 | 77 | 60 | 50 | 120,000 | — | 208 |
| 44 | 2 | MAO/Silica | 240 | TIBA | 0.5 | 77 | 60 | 52 | 125,000 | — | 217 |

TABLE V

| | Molecular Weight Distribution Data (molecular weights in kg/mol) | | | | | | | Properties After Volatile Component Removal | | | |
|---|---|---|---|---|---|---|---|---|---|---|---|
| Ex | Mn | Mw | Mz | Mv | Mp | Mw/Mn | Mz/Mw | VI | Vis 40 (cSt) | Vis 100 (cSt) | Flash Point | Pour Point |
| 34 Crude Product | 0.8 | 1.86 | 3.65 | 1.7 | 1.6 | 2.32 | 1.96 | 92 | 219.8 | 18.34 | 172 | −26 |
| After Volatile Removal | 0.97 | 1.98 | 3.83 | 1.82 | 1.56 | 2.04 | 1.93 | | | | | |
| 35 Crude Product | 0.79 | 1.94 | 3.93 | 1.76 | 1.65 | 2.46 | 2.02 | | | | | |
| After Volatile Removal | 1.03 | 2.09 | 4.00 | 1.93 | 1.65 | 2.03 | 1.91 | | | | | |
| 36 Crude Product | 0.7 | 1.82 | 3.97 | 1.64 | 1.56 | 2.60 | 2.18 | | | | | |
| After Volatile Removal | 1.03 | 2.01 | 3.84 | 1.86 | 1.56 | 1.95 | 1.91 | | | | | |
| 37 Crude Product | | | | | | | | 82 | 1365 | 53.41 | 228 | −10 |
| After Volatile Removal | 1.51 | 2.89 | 4.97 | 2.70 | 2.35 | 1.91 | 1.72 | | | | | |
| 38 Crude Product | | | | | | | | | | | | |
| After Volatile Removal | 1.54 | 3.17 | 9.54 | 2.88 | 2.39 | 2.06 | 3.01 | | | | | |
| 39 Crude Product | 1.32 | 2.81 | 4.85 | 2.62 | 2.35 | 2.13 | 1.73 | | | | | |
| After Volatile Removal | 1.44 | 2.88 | 4.96 | 2.68 | 2.39 | 2.00 | 1.72 | | | | | |
| 40 Crude Product | 1.29 | 2.71 | 4.59 | 2.52 | 2.29 | 2.1 | 1.69 | | | | | |
| After Volatile Removal | 1.46 | 2.77 | 4.63 | 2.59 | 2.35 | 1.90 | 1.67 | | | | | |
| 41 Crude Product | 1.49 | 3.05 | 5.23 | 2.84 | 2.46 | 2.05 | 1.71 | 83 | 5355 | 119.7 | 242 | 0 |
| After Volatile Removal | 1.68 | 3.07 | 5.1 | 2.88 | 2.46 | 1.83 | 1.66 | | | | | |
| 42 Crude Product | | | | | | | | | | | | |
| 42 After Volatile Removal | 1.88 | 4.00 | 7.26 | 3.7 | 3.03 | 2.13 | 1.82 | | | | | |
| 43 Crude Product | | | | | | | | | | | | |
| After Volatile Removal | 1.89 | 4.04 | 7.57 | 3.72 | 2.91 | 2.14 | 1.87 | | | | | |
| 44 Crude Product | | | | | | | | | | | | |
| After Volatile Removal | 2.00 | 4.16 | 7.67 | 3.84 | 3.07 | 2.08 | 1.84 | | | | | |

TABLE VI

| Example | Isotactic (%) | Atactic (%) | Syndiotactic (%) |
|---|---|---|---|
| 34-36 | 26.6 | 46.9 | 26.4 |
| 37-40 | 25.7 | 48.0 | 26.3 |
| 41-44 | 29.3 | 46.7 | 24.0 |

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1. A propylene oligomer having a Mn in a range from 250 to 10,000 g/mol, a viscosity index of at least 85, a pour point in a range from −5 to −60° C.

Embodiment 2. A propylene oligomer having a Mn in a range from 250 to 10,000 g/mol, a ratio of Mz/Mw in a range from 1.9 to 8, and a viscosity index of at least 85.

Embodiment 3. The propylene oligomer defined in embodiment 1 or 2, wherein the propylene oligomer has a Mn in any range of Mn's disclosed herein, e.g., from 250 to 5000 g/mol, from 400 to 7500 g/mol, from 500 to 5000 g/mol, from 500 to 4000 g/mol, from 500 to 2500 g/mol, from 600 to 2500 g/mol, from 750 to 2500 g/mol, etc.

Embodiment 4. The propylene oligomer defined in any one of embodiments 1-3, wherein the propylene oligomer has a pour point in any range of pour points disclosed herein, e.g., from −5 to −50° C., from −5 to −45° C., from −8 to −45° C., from −10 to −40° C., from −10 to −35° C., from −15 to −60° C., from −15 to −50° C., from −15 to −40° C., etc.

Embodiment 5. The propylene oligomer defined in any one of embodiments 1-4, wherein the propylene oligomer has a viscosity index in any range of viscosity indices disclosed herein, e.g., from 85 to 200, from 85 to 175, from 85 to 140, from 85 to 130, from 88 to 150, from 88 to 135, from 90 to 140, from 90 to 130, etc.

Embodiment 6. The propylene oligomer defined in any one of embodiments 1-5, wherein the propylene oligomer has a Mw in any range of Mw's disclosed herein, e.g., from 500 to 10,000 g/mol, from 750 to 9000 g/mol, from 750 to 7000 g/mol, from 1000 to 5000 g/mol, from 500 to 4000 g/mol, from 500 to 3000 g/mol, from 1000 to 5000 g/mol, from 1500 to 5000 g/mol, etc.

Embodiment 7. The propylene oligomer defined in any one of embodiments 1-6, wherein the propylene oligomer has a ratio of Mw/Mn in any range of Mw/Mn ratios disclosed herein, e.g., from 1.6 to 5, from 1.8 to 5, from 1.8 to 4.5, from 1.9 to 4, from 2 to 4, etc.

Embodiment 8. The propylene oligomer defined in any one of embodiments 1-7, wherein the propylene oligomer has a ratio of Mz/Mw in any range of Mz/Mw ratios disclosed herein, e.g., from 1.9 to 8, from 1.9 to 6, from 1.9 to 5, from 1.9 to 3, etc.

Embodiment 9. The propylene oligomer defined in any one of embodiments 1-8, wherein the propylene oligomer has a kinematic viscosity at 100° C. in any range of kinematic viscosities at 100° C. disclosed herein, e.g., from 6 to 200 cSt, from 8 to 150 cSt, from 10 to 150 cSt, from 10 to 100 cSt, from 12 to 150 cSt, from 12 to 100 cSt, from 12 to 80 cSt, from 12 to 60 cSt, from 14 to 50 cSt, etc.

Embodiment 10. The propylene oligomer defined in any one of embodiments 1-9, wherein the propylene oligomer has a kinematic viscosity at 40° C. in any range of kinematic viscosities at 40° C. disclosed herein, e.g., from 25 to 8000 cSt, from 50 to 6000 cSt, from 75 to 6000 cSt, from 75 to 400 cSt, from 25 to 800 cSt, 100 to 6000 cSt, from 100 to 4000 cSt, from 150 to 6000, from 150 to 400 cSt, from 150 to 2000 cSt, from 175 to 2000 cSt, from 175 to 1500 cSt, from 200 to 2000 cSt, from 200 to 1500 cSt, from 200 to 800 cSt, etc.

Embodiment 11. The propylene oligomer defined in any one of embodiments 1-10, wherein the propylene oligomer has a flash point in any range of flash points disclosed herein, e.g., from 140 to 300° C., from 140 to 260° C., from 140 to 220° C., from 140 to 190° C., from 160 to 240° C., from 160 to 200° C., etc.

Embodiment 12. The propylene oligomer defined in any one of embodiments 1-11, wherein the propylene oligomer has a mr triad content in any range of atactic contents disclosed herein, e.g., from 40% to 50%, from 41% to 49%, from 42% to 50%, from 42% to 49%, etc.

Embodiment 13. The propylene oligomer defined in any one of embodiments 1-12, wherein the propylene oligomer comprises any amount of propylene disclosed herein, e.g., at least 98 mol %, at least 98.5 mol %, at least 99 mol %, at least 99.25 mol %, at least 99.5 mol % propylene, etc.

Embodiment 14. The propylene oligomer defined in any one of embodiments 1-13, wherein the propylene oligomer is a liquid at standard temperature and pressure.

Embodiment 15. A hydrogenated propylene oligomer defined in any one of embodiments 1-14.

Embodiment 16. A composition comprising the propylene oligomer defined in any one of embodiments 1-14 or the hydrogenated propylene oligomer defined in embodiment 15.

Embodiment 17. A base oil comprising the comprising the propylene oligomer defined in any one of embodiments 1-14 or the hydrogenated propylene oligomer defined in embodiment 15.

Embodiment 18. A lubricant composition comprising the propylene oligomer defined in any one of embodiments 1-14 or the hydrogenated propylene oligomer defined in embodiment 15.

Embodiment 19. The composition, base oil, or lubricant composition defined in any one of embodiments 16-18, further comprising any suitable additive or any additive disclosed herein, e.g., viscosity index improvers/viscosity modifiers/viscosity improvers, dispersants (metallic and/or non-metallic), detergents (metallic and/or non-metallic), friction modifiers, traction improving additives, demulsifiers, defoamants, antioxidants, anti-wear additives (metallic and non-metallic, phosphorus-containing and non-phosphorus, sulfur-containing and non-sulfur types), extreme-pressure additives (metallic and non-metallic, phosphorus-containing and non-phosphorus, sulfur-containing and non-sulfur types), anti-rust additives, corrosion inhibitors, metal deactivators, anti-seizure agents, pour point depressants, wax modifiers, seal compatibility agents, lubricity agents, anti-staining agents, chromophores (dyes), haze inhibitors, etc., or any combination thereof.

Embodiment 20. A process comprising:
contacting an olefin feedstock comprising propylene with a catalyst system comprising (i) a metallocene compound, (ii) a chemically-treated solid oxide, and (iii) an optional co-catalyst, to form an oligomer product under oligomerization conditions.

Embodiment 21. The process defined in embodiment 20, wherein a composition comprising the olefin feedstock is any suitable composition, e.g., refinery grade propylene, chemical grade propylene, polymer grade propylene, etc., or a composition comprising the olefin feedstock comprises any suitable amount of propylene, $C_1$ to $C_{4+}$ paraffins, and $C_2$ and/or $C_{4+}$ olefins disclosed herein.

Embodiment 22. The process defined in embodiment 20 or 21, wherein the chemically-treated solid oxide can comprise a solid oxide and an electron-withdrawing anion where the solid oxide can comprise any solid oxide disclosed herein, e.g., silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof and the electron-withdrawing anion can comprise any electron-withdrawing anion disclosed herein, e.g., sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or any combination thereof.

Embodiment 23. The process defined in any one of embodiments 20-22, wherein the chemically-treated solid oxide comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Embodiment 24. The process defined in any one of embodiments 20-22, wherein the chemically-treated solid oxide comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof.

Embodiment 25. The process defined in any one of embodiments 20-22, wherein the chemically-treated solid oxide comprises fluorided silica-coated alumina.

Embodiment 26. The process defined in any one of embodiments 20-22, wherein the chemically-treated solid oxide comprises a fluorided solid oxide, a sulfated solid oxide, or any combination thereof.

Embodiment 27. The process defined in any one of embodiments 20-22, wherein the chemically-treated solid oxide further comprises any metal or metal ion disclosed herein, e.g., zinc, nickel, vanadium, titanium, silver, copper, gallium, tin, tungsten, molybdenum, zirconium, or any combination thereof.

Embodiment 28. The process defined in any one of embodiments 20-27, wherein the catalyst system comprises any suitable metallocene compound or any metallocene compound disclosed herein.

Embodiment 29. The process defined in any one of embodiments 20-28, wherein the metallocene compound comprises a bridged zirconium or hafnium based metallocene compound.

Embodiment 30. The process defined in any one of embodiments 20-28, wherein the metallocene compound comprises a bridged zirconium or hafnium based metallocene with a carbon bridging atom or a silicon bridging atom.

Embodiment 31. The process defined in any one of embodiments 20-28, wherein the metallocene compound comprises a bridged zirconium based metallocene with a cyclopentadienyl group and a carbon bridging atom or a silicon bridging atom.

Embodiment 32. The process defined in any one of embodiments 20-28, wherein the metallocene compound comprises a bridged zirconium based metallocene with two cyclopentadienyl groups and a carbon bridging atom or a silicon bridging atom.

Embodiment 33. The process defined in any one of embodiments 20-28, wherein the metallocene compound comprises an unbridged zirconium or hafnium based metallocene compound containing two cyclopentadienyl groups, two indenyl groups, or a cyclopentadienyl group and an indenyl group.

Embodiment 34. The process defined in any one of embodiments 20-28, wherein the metallocene compound comprises an unbridged zirconium or hafnium based metallocene compound containing two cyclopentadienyl groups.

Embodiment 35. The process defined in any one of embodiments 20-28, wherein the metallocene compound comprises an unbridged zirconium based metallocene compound containing two cyclopentadienyl groups.

Embodiment 36. The process defined in embodiment 34 or 35, wherein the cyclopentadienyl groups are alkyl-substituted cyclopentadienyl groups.

Embodiment 37. The process defined in any one of embodiments 20-28, wherein the metallocene compound comprises an unbridged zirconium or hafnium based metallocene compound containing a cyclopentadienyl group and an indenyl group.

Embodiment 38. The process defined in any one of embodiments 20-28, wherein the metallocene compound comprises an unbridged zirconium based metallocene compound containing a cyclopentadienyl group and an indenyl group.

Embodiment 39. The process defined in any one of embodiments 20-28, wherein the metallocene compound comprises an unbridged zirconium based metallocene compound containing a cyclopentadienyl group and an indenyl group with an alkenyl substituent.

Embodiment 40. The process defined in any one of embodiments 20-39, wherein the catalyst system comprises a co-catalyst, e.g., any co-catalyst disclosed herein.

Embodiment 41. The process defined in any one of embodiments 20-40, wherein the co-catalyst comprises an organoaluminum compound, an organozinc compound, an organomagnesium compound, an organolithium compound, or any combination thereof.

Embodiment 42. The process defined in any one of embodiments 20-41, wherein the co-catalyst comprises an organoaluminum compound.

Embodiment 43. The process defined in embodiment 42, wherein the organoaluminum compound comprises any organoaluminum compound disclosed herein, e.g., trimethylaluminum, triethylaluminum, triisobutylaluminum, etc., or combinations thereof.

Embodiment 44. The process defined in any one of embodiments 20-43, wherein the catalyst system is substantially free of aluminoxane compounds, organoboron or organoborate compounds, ionizing ionic compounds, or combinations thereof.

Embodiment 45. The process defined in any one of embodiments 20-43, wherein the co-catalyst comprises an aluminoxane compound, an organoboron or organoborate compound, an ionizing ionic compound, an organoaluminum compound, an organozinc compound, an organomagnesium compound, an organolithium compound, or any combination thereof.

Embodiment 46. The process defined in any one of embodiments 20-45, wherein the catalyst system is produced by a process comprising contacting, in any order, the metallocene compound, the chemically-treated solid oxide, and the co-catalyst.

Embodiment 47. The process defined in any one of embodiments 20-46, wherein a weight ratio of the chemically-treated solid oxide to the metallocene compound is in any range of weight ratios disclosed herein, e.g., from 50:1 to 1500:1, from 50:1 to 1000:1, from 50:1 to 800:1, from 60:1 to 800:1, from 60:1 to 600:1, from 70:1 to 600:1, from 70:1 to 500:1, etc.

Embodiment 48. The process defined in any one of embodiments 20-47, wherein a molar ratio of co-catalyst to metallocene compound is in any range of molar ratios disclosed herein, e.g., from 5:1 to 5000:1, from 5:1 to 1000:1, from 5:1 to 250:1, from 10:1 to 150:1, etc.

Embodiment 49. The process defined in any one of embodiments 20-48, wherein a molar ratio of propylene to the metallocene compound is in any range of weight ratios disclosed herein, e.g., from $1 \times 10^3$:1 to $1 \times 10^9$:1, from $5 \times 10^3$:1 to $1 \times 10^9$:1, from $5 \times 10^3$:1 to $5 \times 10^8$:1, from $1 \times 10^4$:1 to $1 \times 10^8$:1, from $5 \times 10^4$:1 to $1 \times 10^8$:1, from $5 \times 10^4$:1 to $5 \times 10^7$:1, from $1 \times 10^5$:1 to $5 \times 10^7$:1, from $1 \times 10^5$:1 to $1 \times 10^7$:1, from $1 \times 10^5$:1 to $5 \times 10^6$:1, from $1 \times 10^5$:1 to $1 \times 10^6$:1, etc.

Embodiment 50. The process defined in any one of embodiments 20-49, wherein the oligomerization conditions comprise an oligomerization temperature in any oligomerization temperature range disclosed herein, e.g., from 0° C. to 165° C., from 20° C. to 160° C., from 40° C. to 160° C., from 50° C. to 150° C., from 50° C. to 140° C., from 50° C. to 130° C., from 60° C. to 130° C., from 60° C. to 120° C., etc.

Embodiment 51. The process defined in any one of embodiments 20-50, wherein the oligomerization conditions comprise a reaction pressure (or propylene partial pressure) in any range disclosed herein, e.g., from 50 psig (344 KPa) to 4,000 psig (27.6 MPa), from 100 psig (689 KPa) to 3,000 psig (20.9 MPa), from 200 psig (1.4 MPa) to 2,000 psig (13.8 MPa), from 250 psig (1.5 MPa) to 1,500 psig (10.3 MPa), etc.

Embodiment 52. The process defined in any one of embodiments 20-51, wherein the oligomer product is formed in the presence of hydrogen.

Embodiment 53. The process defined in embodiment 52, wherein the oligomer product is formed at a hydrogen partial pressure in any range disclosed herein, e.g., from 1 psig (6.9 kPa) to 2000 psig (13.8 MPa), from 5 psig (34 kPa) to 1500 psig (10.3 MPa), from 10 psig (69 kPa) to 1000 psig (6.9 MPa), from 10 psig (69 kPa) to 500 psig (3.5 MPa), from 25 psig (172 kPa) to 500 psig (3.4 MPa), etc.

Embodiment 54. The process defined in embodiment 52 or 53, wherein the catalyst system is responsive to hydrogen addition, e.g., the decrease in the Mn of the oligomer product produced by the process in the presence of hydrogen is greater than the decrease in the Mn of an oligomer product produced by a catalyst system containing an aluminoxane activator (e.g., MAO) instead of the chemically-treated solid oxide, under the same oligomerization conditions.

Embodiment 55. The process defined in any one of embodiments 20-51, wherein the oligomer product is formed in the substantial absence of hydrogen (e.g., no added hydrogen).

Embodiment 56. The process defined in any one of embodiments 20-55, wherein the activity of the catalyst system is at least 25,000, 30,000, 35,000, or 40,000 grams of oligomer product per gram of metallocene per hour; additionally or alternatively, the activity of the catalyst system is at least 2,000, 4,000, 5,000 or 6,000 grams of oligomer product per gram of co-catalyst per hour.

Embodiment 57. The process defined in any one of embodiments 20-56, wherein the oligomer product is formed in a reaction system comprising a fixed bed reactor, a stirred tank reactor, a plug flow reactor, or a combination thereof.

Embodiment 58. The process defined in any one of embodiments 20-57, wherein the process further comprises a step of deactivating the catalyst system using any suitable technique or any technique disclosed herein.

Embodiment 59. The process defined in any one of embodiments 20-58, wherein the process further comprises a step of separating unreacted monomer (e.g., propylene) and the oligomer product from the catalyst system or deactivated catalyst system using any suitable technique or any technique disclosed herein, e.g., filtration, etc.

Embodiment 60. The process defined in any one of embodiments 20-59, wherein the process further comprises isolating a heavy propylene oligomer by a step of removing unreacted propylene and at least a portion of the light propylene oligomers (e.g., $C_6$-$C_{12}$, etc.) from the oligomer product using any suitable technique or any technique disclosed herein, e.g., flash processes, distillations processes, as well as combinations thereof.

Embodiment 61. The process of embodiment 60, wherein the heavy propylene oligomer has a flash point in any range of flash points disclosed herein, e.g., from 140 to 300° C., from 140 to 220° C., from 160 to 240° C., or from 160 to 200° C.

Embodiment 62. The process defined in any one of embodiments 20-61, wherein the oligomer product or the heavy propylene oligomer has the properties of the propylene oligomer defined in any one of embodiments 1-14.

Embodiment 63. The process defined in any one of embodiments 20-62, wherein the process further comprises a step of hydrogenating the oligomer product or the heavy propylene oligomer using any suitable technique or any technique disclosed herein.

Embodiment 64. The process of embodiment 63, wherein the hydrogenated oligomer product or the hydrogenated heavy propylene oligomer has the properties of the hydrogenated propylene oligomer defined in embodiment 15.

Embodiment 65. A heavy propylene oligomer or hydrogenated heavy propylene oligomer produced by the process defined in any one of embodiments 20-64.

Embodiment 66. A composition comprising the heavy propylene oligomer or hydrogenated heavy propylene oligomer defined in embodiment 65.

Embodiment 67. A base oil comprising the heavy propylene oligomer or hydrogenated heavy propylene oligomer defined in embodiment 65.

Embodiment 68. A lubricant composition comprising the heavy propylene oligomer or hydrogenated heavy propylene oligomer defined in embodiment 64 or 65, or the base oil defined in embodiment 67.

Embodiment 69. The lubricant composition defined in embodiment 68, further comprising any suitable additive or any additive disclosed herein, as well as combinations thereof.

We claim:

1. A propylene oligomer having:
    a Mn in a range from 250 to 10,000 g/mol;
    a kinematic viscosity at 100° C. in a range from 6 to 200 cSt;
    a kinematic viscosity at 40° C. in a range from 25 to 8000 cSt;
    a viscosity index of at least 85; and
    a pour point in a range from −5 to −60° C.

2. The oligomer of claim 1, wherein the propylene oligomer has:
    a Mn in a range from 500 to 5000 g/mol;
    a viscosity index in a range from 85 to 175; and
    a pour point in a range from −10 to −35° C.

3. The oligomer of claim 1, wherein the propylene oligomer has:
    a Mn in a range from 500 to 2500 g/mol;
    a viscosity index in a range from 88 to 135; and
    a pour point in a range from −15 to −40° C.

4. The oligomer of claim 1, wherein the propylene oligomer has:
    a kinematic viscosity at 100° C. in a range from 8 to 250 cSt;
    a kinematic viscosity at 40° C. in a range from 50 to 6000 cSt; and
    a flash point in a range from 140 to 300° C.

5. The oligomer of claim 1, wherein the propylene oligomer has:
    a kinematic viscosity at 100° C. in a range from 12 to 80 cSt;
    a kinematic viscosity at 40° C. in a range from 200 to 1500 cSt; and
    a flash point in a range from 160 to 200° C.

6. The oligomer of claim 1, wherein the propylene oligomer comprises at least 98 mol % propylene.

7. The oligomer of claim 1, wherein the propylene oligomer comprises at least 99.5 mol % propylene.

8. The oligomer of claim 1, wherein the propylene oligomer is a liquid at standard temperature and pressure.

9. The oligomer of claim 1, wherein the propylene oligomer is a hydrogenated propylene oligomer.

10. A base oil or lubricant composition comprising the propylene oligomer of claim 1.

11. A propylene oligomer having:
a Mn in a range from 250 to 10,000 g/mol;
a ratio of Mz/Mw in a range from 1.9 to 8;
a kinematic viscosity at 100° C. in a range from 6 to 200 cSt;
a kinematic viscosity at 40° C. in a range from 25 to 8000 cSt; and
a viscosity index of at least 85.

12. The oligomer of claim 11, wherein the propylene oligomer has:
a Mn in a range from 500 to 5000 g/mol;
a ratio of Mz/Mw in a range from 1.9 to 6; and
a viscosity index in a range from 85 to 175.

13. The oligomer of claim 11, wherein the propylene oligomer has:
a kinematic viscosity at 100° C. in a range from 12 to 80 cSt;
a kinematic viscosity at 40° C. in a range from 200 to 1500 cSt; and
a flash point in a range from 160 to 200° C.

14. A base oil or lubricant composition comprising the propylene oligomer of claim 11.

15. A process comprising:
contacting an olefin feedstock comprising propylene with a catalyst system comprising (i) a metallocene compound, (ii) a chemically-treated solid oxide, and (iii) an optional co-catalyst, to form an oligomer product under oligomerization conditions; and
isolating the propylene oligomer of claim 1 from the oligomer product.

16. The process of claim 15, wherein the olefin feedstock comprising propylene is contacted with the catalyst system in the presence of hydrogen, and wherein the catalyst system comprises an organoaluminum co-catalyst.

17. The process of claim 16, wherein a decrease in the Mn of the oligomer product produced by the process in the presence of hydrogen is greater than a decrease in the Mn of an oligomer product produced by a catalyst system comprising an aluminoxane activator instead of the chemically-treated solid oxide, under the same oligomerization conditions.

18. The process of claim 15, wherein the chemically-treated solid oxide comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof.

19. The process of claim 15, wherein an activity of the catalyst system is at least 25,000 grams of the oligomer product per gram of the metallocene compound per hour.

20. The process of claim 15, wherein isolating comprises removing unreacted propylene and at least a portion of light propylene oligomers from the oligomer product using one or more separation steps.

21. The oligomer of claim 2, wherein:
the propylene oligomer comprises at least 98 mol % propylene; and
the propylene oligomer has a kinematic viscosity at 100° C. in a range from 12 to 80 cSt.

22. A base oil or lubricant composition comprising the propylene oligomer of claim 21.

23. The oligomer of claim 3, wherein:
the propylene oligomer comprises at least 99.5 mol % propylene; and
the propylene oligomer has a kinematic viscosity at 100° C. in a range from 12 to 80 cSt.

24. The oligomer of claim 12, wherein:
the propylene oligomer comprises at least 98 mol % propylene; and
the propylene oligomer has a kinematic viscosity at 100° C. in a range from 12 to 80 cSt.

25. A base oil or lubricant composition comprising the propylene oligomer of claim 24.

* * * * *

UNITED STATES PATENT AND TRADEMARK OFFICE
CERTIFICATE OF CORRECTION

PATENT NO. : 9,732,300 B2  
APPLICATION NO. : 14/806708  
DATED : August 15, 2017  
INVENTOR(S) : Uriah J. Kilgore et al.

Page 1 of 1

It is certified that error appears in the above-identified patent and that said Letters Patent is hereby corrected as shown below:

On the Title Page

Item (73), Assignee:
"Chevron Phillipa Chemical Company LP" should be changed to -- Chevron Phillips Chemical Company LP --

Signed and Sealed this  
Twenty-fourth Day of April, 2018

Andrei Iancu  
*Director of the United States Patent and Trademark Office*